(12) United States Patent
Palazzolo et al.

(10) Patent No.: US 8,275,634 B2
(45) Date of Patent: *Sep. 25, 2012

(54) METHOD AND SYSTEM FOR ALIGNING A PLURALITY OF PRESCRIPTION REFILLS TO MULTIPLE ALIGNMENT DATES

(75) Inventors: Christina M. Palazzolo, Chicago, IL (US); Greg Pankow, Morton Grove, IL (US); Gyula Jozsef Nadas, Wauconda, IL (US); Hee Kyu Oh, Wilmette, IL (US); Peter Liccardo, Evanston, IL (US); Laura Jean Tebbe, Antioch, IL (US); Guirong Zhou Webb, Vernon Hills, IL (US); Steve Scott Dorfman, Chicago, IL (US); Rishi Khullar, Deerfield, IL (US)

(73) Assignee: Walgreen Co., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,769

(22) Filed: Aug. 22, 2011

(65) Prior Publication Data
US 2012/0004929 A1    Jan. 5, 2012

Related U.S. Application Data

(63) Continuation of application No. 11/781,945, filed on Jul. 23, 2007, now Pat. No. 8,005,689.

(51) Int. Cl.
*G06Q 50/00* (2012.01)
(52) U.S. Cl. ............................................... 705/2; 705/3
(58) Field of Classification Search .................. 705/2–4; 600/300–301
See application file for complete search history.

(56) References Cited

U.S. PATENT DOCUMENTS

| | | | |
|---|---|---|---|
| 5,845,255 A | 12/1998 | Mayaud | |
| 6,493,427 B1 | 12/2002 | Kobylevsky et al. | |
| 7,126,879 B2 | 10/2006 | Snyder | |
| 7,286,996 B1 | 10/2007 | Fiedotin et al. | |
| 7,426,476 B2 * | 9/2008 | Munoz et al. | 705/3 |
| 7,702,525 B2 | 4/2010 | Kosinski et al. | |
| 7,835,924 B1 | 11/2010 | Palazzolo et al. | |
| 7,856,363 B2 | 12/2010 | Palazzolo et al. | |
| 7,996,243 B1 | 8/2011 | Ali et al. | |
| 8,005,689 B2 | 8/2011 | Palazzolo et al. | |
| 8,032,393 B2 | 10/2011 | Palazzolo et al. | |
| 8,050,942 B1 | 11/2011 | Ali et al. | |
| 2002/0032582 A1 | 3/2002 | Feeney et al. | |

(Continued)

OTHER PUBLICATIONS

Salganie, M. William, "A Pill on Time Seems to Help the Bottom Line", Sep. 9, 2002, The Baltimore Sun, Business.*

(Continued)

*Primary Examiner* — Gerald J. O'Connor
*Assistant Examiner* — Edward Winston, III
(74) *Attorney, Agent, or Firm* — Francis C. Kowalik; Marshall, Gerstein & Borun LLP; Randall G. Rueth

(57) ABSTRACT

The method, system and user-interface allows alignment of refill dates associated with a plurality of prescriptions to a plurality of alignment dates, such that a plurality of selected prescriptions require refills on each of the plurality of alignment dates, thus limiting the number of occasions on which a customer must visit the pharmacy to retrieve refills of the aligned prescriptions, and increasing the likelihood that the customer will comply with the recommended medication regimen.

10 Claims, 12 Drawing Sheets

U.S. PATENT DOCUMENTS

2003/0149599 A1    8/2003    Goodall et al.

OTHER PUBLICATIONS

Office action for U.S. Appl. No. 12/942,779 dated Nov. 17, 2011.
Office action for U.S. Appl. No. 11/781,926 dated Feb. 11, 2011.
Office action for U.S. Appl. No. 12/900,728 dated Nov. 22, 2011.
Salagnie, "A Pill on Time Seems to Help the Bottom Line," The Baltimore Sun, Business, Sep. 9, 2002, 1 page.
U.S. Appl. No. 12/694,968 entitled "Method and System for Calculating an Alignment Date for Prescriptions," filed Jan. 27, 2010.
U.S. Appl. No. 12/694,974 entitled "Method and System for Charging Customers for Prescription Alignment," filed Jan. 27, 2010.
U.S. Appl. No. 12/900,728 entitled "Method and System for Delivering to a Customer a Plurality of Prescriptions Having Aligned Refill Dates," filed Oct. 8, 2010.
U.S. Appl. No. 12/942,779 entitled "Method and System for Aligning a Plurality of Refill Dates for Prescriptions Associated with a Plurality of Customers" filed Nov. 9, 2010.

* cited by examiner

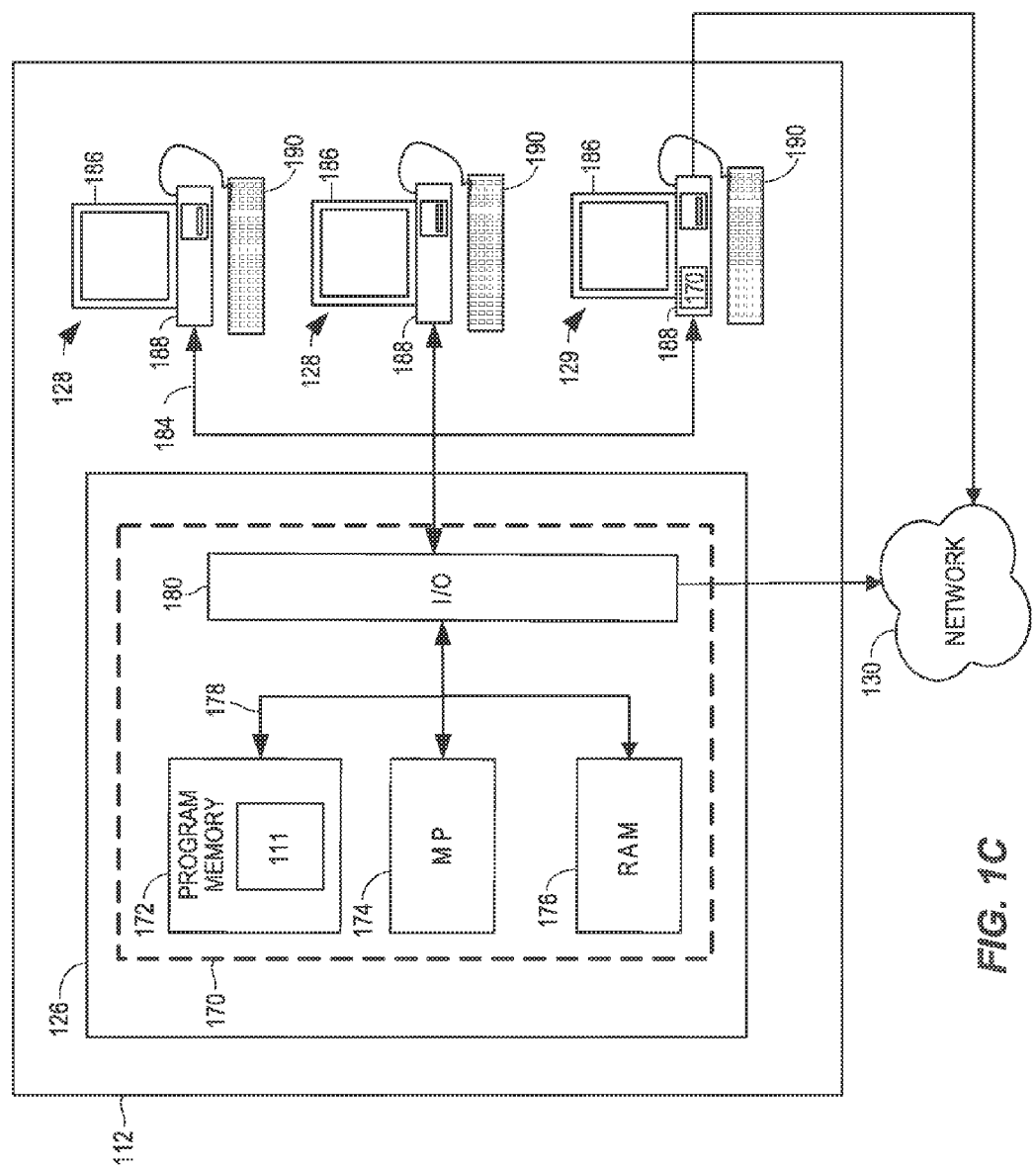

Prescription Alignment for DOE, JANE — 802

804 — Wednesday, July 18, 2007

Printable Version | Contact Us | Tips | Help — 890

Step 1 of 2: Active Prescriptions

Please Select the Prescriptions to Align

| | Prescription Number | Store Number | Medication Name | Last Fill Date | Day Supply | Refills Remaining |
|---|---|---|---|---|---|---|
| ☒ Select All — 875 | | | | | | |
| ☒ | 013579 | 8256 | Generic A 100 MG Tablets | 7/2/2007 | 30 | 10 |
| ☒ | 024680 | 8256 | Brand B 10 MG Capsules | 6/20/2007 | 60 | 5 |
| ☒ | 012345 | 4793 | Generic C 500 MG Capsules | 6/29/2007 | 60 | 5 |
| ☒ | 086420 | 4745 | Generic D 5 MG Capsules | 7/2/2007 | 28 | 11 |
| ☒ | 975310 | 7581 | Generic E 100 MG Tablets | 7/7/2007 | 90 | 3 |
| ☐ Override — 817 | 555121 | 6584 | Brand F 100 MG Tablets | 7/18/2007 (Today) | 30 | 1 |

[ Continue ]   [ Cancel ] — 835

Prescription Alignment for DOE, JANE — 902

904 — Wednesday, July 18, 2007
970 — Printable Version | Contact Us | Tips | Help Step 2 of 2: Alignment Verification and Confirmation Please review the alignment result with the patient. This report is based on the fastest alignment option. — 950
For the lowest cost option, Click Here. — 965

Below is the plan for the alignment of your prescriptions. Your alignment date will be October 5, 2007. You will receive a reduced fill for some of your medications until your alignment date. On October 5, 2007, each of the prescriptions below will be filled and switched to a 90-day supply. — 955
Medications that are not eligible are not included.

| Store Number | Drug Name | Last Fill Date | Quantity | Day Supply | Alignment Information |||
| --- | --- | --- | --- | --- | --- | --- | --- |
| | | | | | Next Fill Date | Reduced-Fill Date | Reduced-Fill Day Supply | Reduced-Fill Co-Pay |
| 8256 | Generic A  100 MG Tablets | 7/2/2007 | 60 | 30 | 8/1/2007 | 9/30/2007 | 5 | $10.00 |
| 8256 | Brand B  10 MG Capsules | 6/20/2007 | 180 | 60 | 8/19/2007 | 8/19/2007 | 47 | $20.00 |
| 4793 | Generic C  500 MG Tablets | 6/29/2007 | 60 | 60 | 8/28/2007 | 8/28/2007 | 38 | $10.00 |
| 4745 | Generic D  5 MG Capsules | 7/2/2007 | 56 | 90 | 7/31/2007 | 9/25/2007 | | |
| 7591 | Generic E  100 MG Tablets | 7/7/2007 | 90 | 90 | 10/5/2007 | | 10 | $10.00 |

Customize Date — 932

Alignment Date: 10/5/2007
Pre-Alignment Cost (90 days): $85.00
Post-Alignment Cost (90 days): $60.00
Add'l Cost Due to Alignment: $50.00
Total Day Supply: 360

Post-Alignment Day Supply: 90    Edit

Default Store: 8256 ▼

Confirm    Change Drugs    Cancel

METHOD AND SYSTEM FOR ALIGNING A PLURALITY OF PRESCRIPTION REFILLS TO MULTIPLE ALIGNMENT DATES

RELATED APPLICATIONS

This application is a continuation of U.S. patent application No. 11/781,945, filed on Jul. 23, 2007, and entitled "METHOD AND SYSTEM FOR ALIGNING A PLURALITY OF PRESCRIPTION REFILLS TO MULTIPLE ALIGNMENT DATES," the entirety of which is hereby incorporated herein by reference for all purposes.

FIELD OF THE INVENTION

The present disclosure generally relates to a process for aligning to a plurality of dates the fill dates for a plurality of prescriptions.

BACKGROUND

Generally, prescription medication orders are filled on the day on which they are written, or shortly thereafter. Because prescriptions may be written at different times, and for different quantities of medication, it is common for a customer with multiple prescriptions to run out of the prescribed medications at varying times. Ordering, and picking up, refills for the various prescriptions at different times may be an inconvenience for a customer where the store location is not convenient, where a customer depends on others to pick up the prescription, or where a customer's schedule does not coincide with the pharmacy schedule. Additionally, many customers may be unable to remember multiple dates on which prescription refills must be ordered or picked up. This may affect the customer's health, as it may lead to missed or skipped doses of medication. While individual pharmacists may be able to manually align a group of prescriptions for an individual customer, the process is time-consuming and inefficient. There is currently no system for aligning prescriptions quickly and efficiently.

SUMMARY OF THE INVENTION

The disclosed method and system provide quick and efficient generation of prescription alignment plans, thereby enabling one or more pharmacists to align the refill dates of a plurality of prescriptions associated with a customer, decreasing the burden placed on the customer by having to remember to refill each prescription, and decreasing the frequency with which the customer must visit the pharmacy to pick up the refilled prescriptions.

The disclosed method and system determines customer eligibility vis-à-vis applicable regulations, the rules of any third-party payors, and the individual prescriptions associated with the customer. If the customer is eligible for prescription alignment, the pharmacist or the system selects a plurality of eligible prescriptions to be aligned. The system may calculate and schedule alignment based on a lowest cost option, a quickest alignment option, or a custom date option. Additionally, the system may calculate and schedule alignment based on the status of the medication as generic or brand name. The system calculates and schedules refill dates, including dates of reduced fills, between the date of the alignment request and the selected alignment date. On the selected alignment date, each of the selected prescriptions is filled with a supply of medication to last the same number of days.

In one alternative embodiment, the system may align a plurality of prescriptions associated with a plurality of customers, such that prescriptions may be aligned that are associated with members of a family, members of a household, or any other group where prescription alignment would lead to decreased effort for the customer and/or increased compliance with medication regimes.

In another alternative embodiment, a plurality of prescriptions may be aligned to multiple dates. A multi-date alignment regime may, for example, allow a customer to better manage the costs associated with a plurality of prescriptions, or may further allow a plurality of prescriptions to be brought into alignment in sub-groups, such that if a final alignment date is in the distant future, smaller groups of prescriptions may be aligned before the final alignment date.

In yet another alternative embodiment, the customer may choose the method by which he/she receives the plurality of aligned prescriptions. The customer may have the plurality of prescriptions delivered, by courier, postal service, or other package service. Where a customer selects delivery, the method allows a central distribution facility to fill the prescriptions, thus eliminating the burden on individual retail locations and decreasing supply-chain management complexity. Further, the central distribution facility may be a third-party, unrelated to the chain of retail pharmacies at which the customer requested prescription alignment.

BRIEF DESCRIPTION OF THE DRAWINGS

FIGS. 1A-1C illustrate block diagrams of a computer network, a computer server, and computing terminals on which an exemplary prescription alignment system may operate in accordance with the described embodiments;

FIG. 6-7 illustrate a schedule of prescription fill dates for a plurality of prescriptions before and after the exemplary prescription alignment process, respectively;

FIGS. 8-9 illustrate an exemplary user-interface for use in a prescription alignment system.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1A:
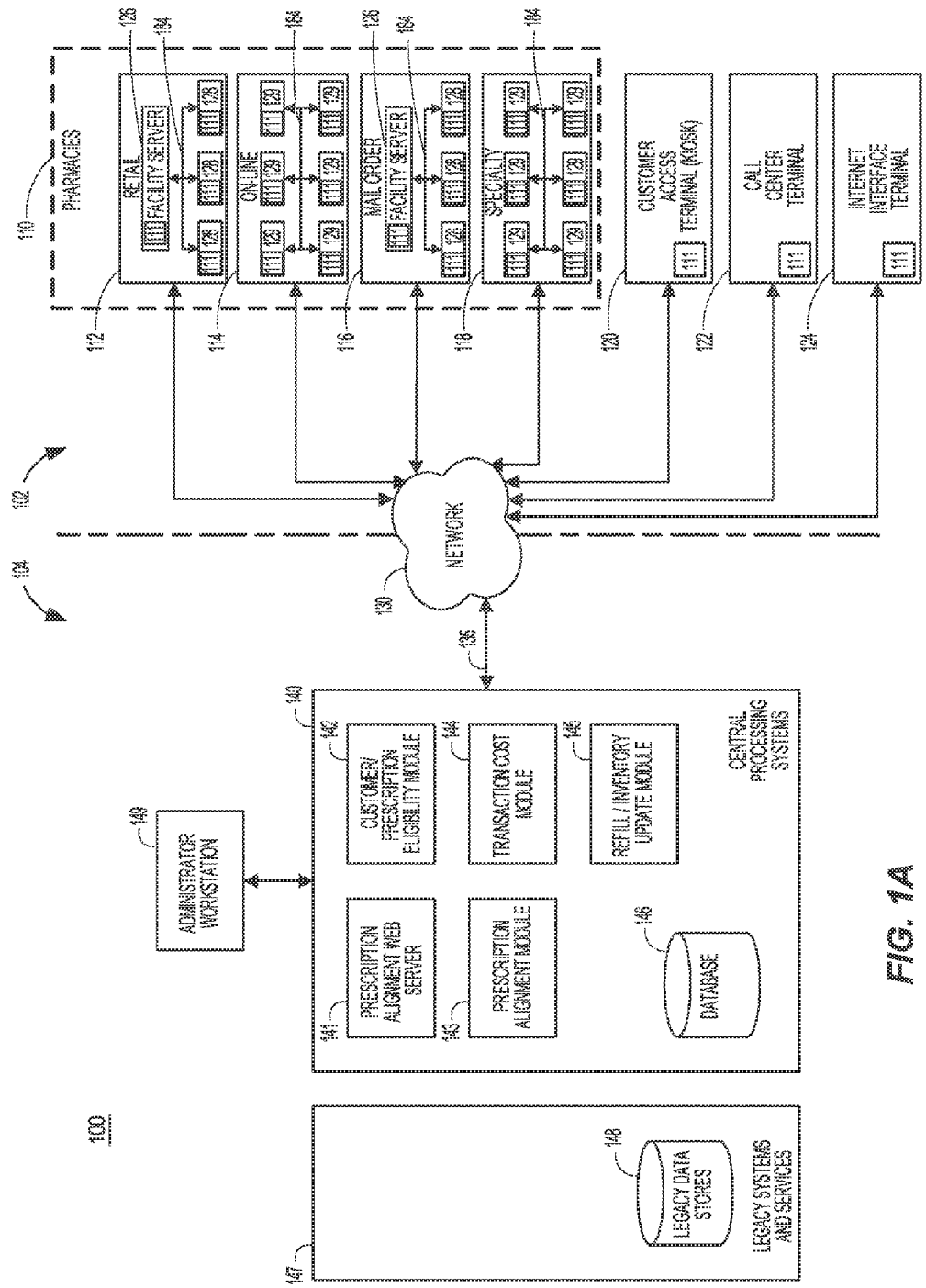

FIG. 1A illustrates a block diagram of an exemplary prescription alignment system 100. The high-level architecture includes both hardware and software applications, as well as various data communications channels for communicating data between the various hardware and software components. The prescription alignment system 100 may be roughly divided into front-end components 102 and back-end components 104. The front-end components 102 are disposed within a plurality of pharmacies 110. The plurality of pharmacies 110 may be located, by way of example rather than limitation, in separate geographic locations from each other, including different areas of the same city or different states. The front-end components 102 comprise a plurality of pharmacy workstations 129. The pharmacy workstations 129 are local computers located in the various pharmacies 110 and executing various pharmacy management-related applications. Pharmacists (not shown) use the pharmacy workstations 129 to access customer information, enter new prescriptions, access insurance and payment information and so forth. Thus, the front-end components 102 may include a plurality of pharmacy workstations 129 for servicing customers visiting a in-store retail pharmacy 112, a plurality of pharmacy workstations 129 for servicing customers who choose to fill their prescriptions through an on-line pharmacy 114, a plurality of pharmacy workstations 129 for servicing customers who prefer to use the services of a mail-order pharmacy 116, and a plurality of pharmacy workstations 129 for servicing customers who require the services of a specialty pharmacy 118.

Those of ordinary skill in the art will recognize that the front-end components 102 could also comprise a plurality of facility servers 126 and client device terminals 128 disposed at the plurality of pharmacies 110, instead of or in addition to a plurality of pharmacy workstations 129. Each pharmacy 112, 114, 116, 118 may include one or more facility servers 126 that may be utilized to facilitate communications between the client device terminals 128 and the back-end components 104 via a network 130, described below, and to store information for a plurality of customers/employees/accounts/etc. associated with each facility. Further, each pharmacy 112, 114, 116, 118 may include one or more client device terminals 128 operatively connected to the facility server 126 via a local network 184. Unless otherwise indicated, any discussion of workstations 129 also refers to facility servers 126 and client device terminals 128, and vice versa.

The front-end components 102 communicate with the back-end components 104 via the network 130. The network 130 may be a proprietary network, a secure pubic internet, a virtual private network or some other type of network, such as dedicated access lines, plain ordinary telephone lines, satellite links, combinations of these, etc. Where the network 130 comprises the Internet, data communication may take place over the network 130 via an Internet communication protocol. The back-end components 104 include prescription alignment central processing systems 140 and legacy systems 147. The legacy systems 147 include legacy data stores (e.g., a database) 148. The legacy systems 147 execute software applications and store data supporting the operation of the front-end components 102. The prescription alignment central processing systems 140 may include one or more computer processors adapted and configured to execute various software applications and components of the prescription alignment system, in addition to other software applications, such as a medication management system. The central processing systems 140 further include a prescription alignment database 146. The prescription alignment database 146 is adapted to store data related to the operation of the prescription alignment system 100. The central processing systems 140 may access data stored in the prescription alignment database 146, as well as data stored in the legacy data stores 148 when executing various functions and tasks associated with the operation of the prescription alignment system 100.

Although the prescription alignment system 100 is shown to include one prescription alignment central processing system 140, one legacy system 147, and four pharmacies 112, 114, 116, and 118, it should be understood that different numbers of computers and pharmacies may be utilized. For example, the system 100 may include a plurality of central processing systems 140 and legacy systems 147, and hundreds of pharmacies 110, all of which may be interconnected via the network 130. According to the disclosed example, this configuration may provide several advantages, such as, for example, enabling near real-time uploads and downloads of information as well as periodic uploads and downloads of information. This provides for a primary backup of all the information generated in the process of updating and accumulating pharmacy data.

Figure 1B:
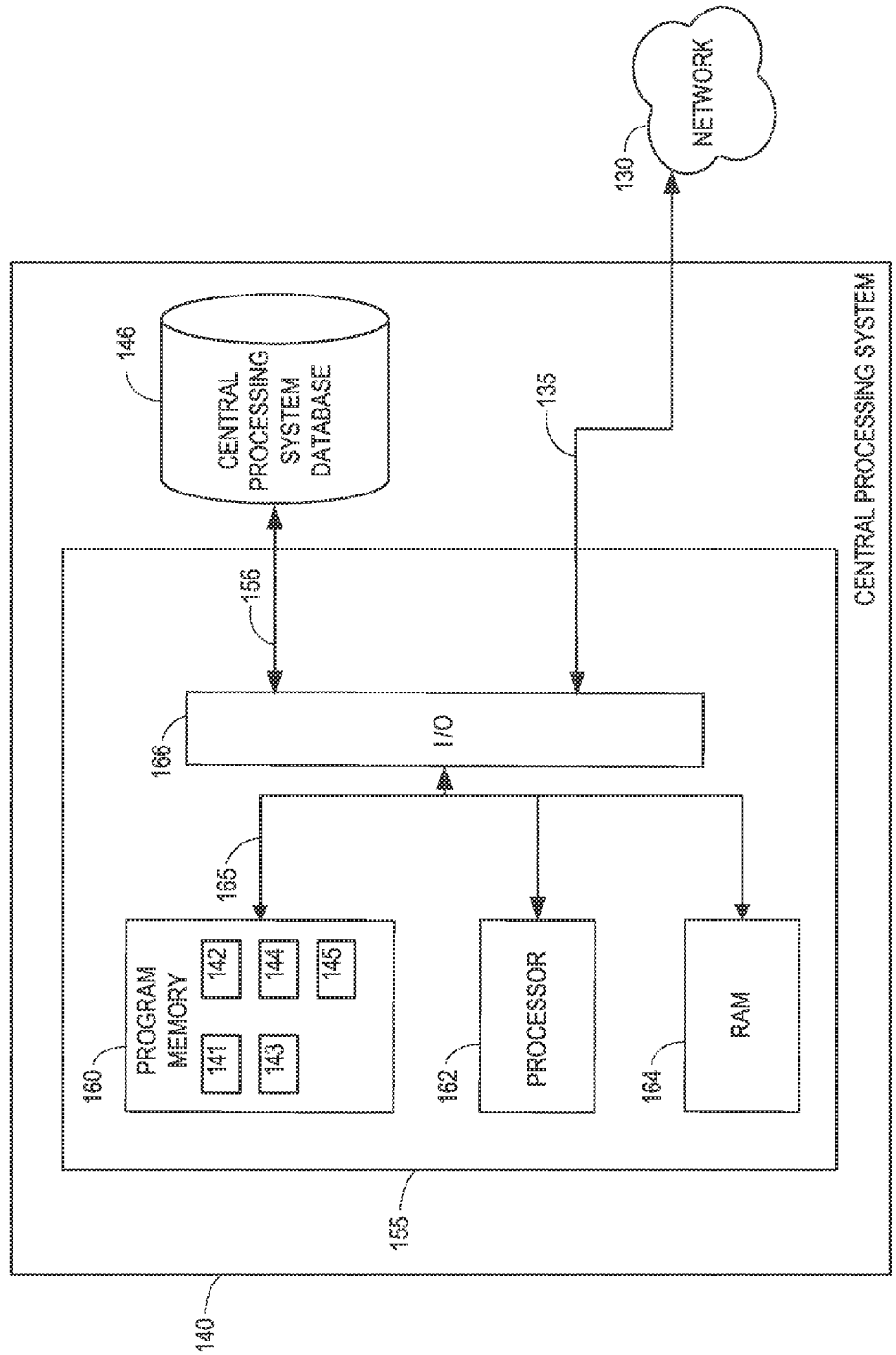

FIG. 1B is a schematic diagram of one possible embodiment of the central processing system 140, or the legacy system 147, shown in FIG. 1A. The central processing system 140, or the legacy system 147, may have a controller 155 that is operatively connected to the database 146 or 148 via a link 156. It should be noted that, while not shown, additional databases may be linked to the controller 155 in a known manner.

The controller 155 may include a program memory 160, a processor 162 (may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and program memories 160 may be implemented as semiconductor memories, magnetically readable memories, and/or optically readable memories, for example. The controller 155 may also be operatively connected to the network 130 via a link 135.

FIG. 1C is a schematic diagram of one possible embodiment of the front-end components 102 located in one or more of the pharmacies 110 from FIG. 1A. Although the following description addresses the design of the pharmacies 110, it should be understood that the design of one or more of the pharmacies 110 may be different than the design of other pharmacies 110. Also, each of the pharmacies 110 may have various different structures and methods of operation. It should also be understood that the embodiment shown in FIG. 1C illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 110 may have one or more pharmacy workstations 129 or a facility server 126. The facility server 126 is operatively connected to a plurality of client device terminals 128 via a network 184. The network 184 also serves to operatively connect a plurality of workstations 129, where workstations are implemented. The network 184 may be a wide area network (WAN), a local area network (LAN), or any other type of network readily known to those persons skilled in the art. The facility server 126, client device terminals 128 or workstations 129 may also be operatively connected to the prescription alignment central processing systems 140 from FIG. 1A via the network 130.

Each workstation 129, client device terminal 128 or facility server 126 includes a controller 170. Similar to the controller 155 from FIG. 1B, the controller 170 may include a program memory 172, a microcontroller or a microprocessor (MP) 174, a random-access memory (RAM) 176, and an input/output (I/O) circuit 180, all of which may be interconnected via an address/data bus 178. As discussed with reference to the controller 155, it should be appreciated that although only one microprocessor 174 is shown, the controller 170 may include multiple microprocessors 174. Similarly, the memory of the controller 170 may include multiple RAMs 176 and multiple program memories 172. Although the I/O circuit 180 is shown as a single block, the I/O circuit 180 may include a number of different types of I/O circuits. The RAM(s) 176 and programs memories 172 may also be implemented as semiconductor memories, magnetically readable memories, and/or optically readable memories, for example.

The client device terminals 128 and workstations 129 may further include a display 186, a keyboard 190 as well as a variety of other input/output devices (not shown) such as a scanner, printer, mouse, touch screen, track pad, track ball, isopoint, voice recognition system, digital camera, etc. Each client device terminal 128 or workstation 129 may be signed onto and occupied by a pharmacy employee to assist them in performing their duties. Pharmacy employees may sign onto a client device terminal 128 or workstation 129 using any generically available technique, such as entering a user name and password. If a pharmacy employee is required to sign onto a client device terminal 128, this information may be passed via the link 184 to the facility server 126, so that the controller 170 will be able to identify which pharmacy employees are signed onto the system and which client device terminals 128 the employees are signed onto. This may be useful in monitoring the pharmacy employees' productivity.

FIG. 1A also illustrates a kiosk or customer access terminal 120 that may form a portion of the prescription alignment system 100. As used herein, the term "customer access terminal" is hereby defined to mean any sort of terminal or kiosk capable of receiving and providing data associated with a prescription, a patient, or a customer. The customer access terminal 120 may be directly coupled to the network 130 or, alternatively, may be a client device terminal 128 coupled to a facility server 126, as illustrated in FIG. 1C. The customer access terminal 120, like the workstation 129, may include a display 186, a controller 170, a keyboard 190 as well as a variety of other input/output devices such as a scanner, credit card reader, printer, mouse, touch screen, track pad, track ball, isopoint, voice recognition system, digital camera, electronic storage device reader (e.g., flash drive interface or magnetic media reader), etc. Each customer access terminal 120 may be placed at any location that provides a suitable connection to the network 130, and not need not necessarily be located at a pharmacy location. The customer access terminal 120 may be accessed by any customer. Although only one customer access terminal 120 is illustrated in FIG. 1A, a plurality of customer access terminals 120 may be connected to the network 130.

A call center terminal 122, also depicted in FIG. 1A, may likewise form a portion of the prescription alignment system 100. As used herein, the term "call center terminal" is hereby defined to mean any sort of terminal not located at a pharmacy, operated by someone other than the customer, and capable of receiving and providing data associated with a prescription, a patient, or a customer. For example, a call center terminal 122 may be disposed within a call center, or other such facility, where one or more operators receive information from customers over a telephone. The call center terminal 122 may be directly coupled to the network 130 or, alternatively, may be a client device terminal 128 coupled to a facility server 126, as illustrated in FIG. 1C. The call center terminal 122 may, like the workstation 129 include a display 186, a controller 170, a keyboard 190 as well as a variety of other input/output devices such as a scanner, credit card reader, printer, mouse, touch screen, track pad, track ball, isopoint, voice recognition system, digital camera, electronic storage device reader (e.g., flash drive interface or magnetic media reader), etc. Although only one call center terminal 122 is illustrated in FIG. 1A, a plurality of call center terminals 122 may be connected to the network 130.

FIG. 1A also illustrates an Internet interface terminal 124 operatively coupled to the prescription alignment system 100 via the network 130. As used herein, the term "Internet interface terminal" is hereby defined to mean any sort of terminal that allows a customer using the terminal to access the data network via the Internet, using an Internet communication protocol (e.g., hypertext transfer protocol, file transfer protocol, etc.), and capable of receiving and providing data associated with a prescription, a patient, or a customer. For example, an Internet interface terminal 124 may be disposed in a customer's home, a physician's office, or any other appropriate location. The Internet interface terminal 124, like the workstation 129, may include a display 186, a controller 170, a keyboard 190 as well as a variety of other input/output devices such as a scanner, credit card reader, printer, mouse, touch screen, track pad, track ball, isopoint, voice recognition system, digital camera, electronic storage device reader (e.g., flash drive interface or magnetic media reader), etc. Although only one Internet interface terminal 124 is illustrated in FIG. 1A, a plurality of Internet interface terminals 124 may be connected to the network 130.

Those of ordinary skill in the art should recognize that there may be overlap between the various types of front-end components 102 employed in the prescription alignment system 100. By way of example and not limitation, a call center terminal 122 located in a call center (not shown), or a client device 128 located at a pharmacy 110, may function as an Internet interface terminal 124, transmitting data to and receiving data from the prescription alignment central processing system 140 using an Internet communication protocol over the network 130. In such instance, a call center operator may use the call center terminal 122 to access the Internet over the network 130, and view or enter customer data via a web page. For this purpose, the prescription alignment central processing systems 140 may include a prescription alignment web server 141. Those of ordinary skill in the art will appreciate that the prescription alignment web server 141 may be a stand-alone server, or a software module implemented within the prescription alignment system 140.

The various front-end equipment 102 may include a web browser client application 111. The prescription alignment web server 141 transmits web pages to the various front-end equipment 126, 128 and 129 in response to URL requests received by the prescription alignment web server 141 from the front-end equipment 102 over the network 130. The web pages sent to the front-end equipment 102 may include data pulled from the prescription alignment database 146, as well as data pulled from the legacy data stores 148. It should be noted that, while the current embodiment describes a web server 141 and a web browser client 111, each implementing the hyper-text transfer protocol, the server 141 could implement any known protocol compatible with the client application 111 running on the front-end equipment 102 and adapted to the purpose of receiving and providing the necessary customer information via the network 130.

The central processing systems 140 may further include a number of software applications. The various software applications are responsible for generating the data content to be included in the web pages sent from the prescription alignment web server 141 to the various front-end equipment 102. The software applications may be executed on the same computer processor as the web server application 141, or on different computer processors. The prescription alignment system 100 may also rely on software applications executed by legacy systems 147 when the legacy systems 147 include functionality that may be beneficial to incorporate into the prescription alignment system 100. Prescription alignment applications may include, by way of example and not limitation, a customer/prescription eligibility module 142 for determining whether a given prescription is eligible for alignment and whether any associated insurance company and any regulating body allow the processes required to align prescriptions, a prescription alignment module 143 for performing the calculations necessary to align prescriptions, a transaction cost module 144 for calculating the costs associated with aligning prescriptions, and a refill/inventory update module 145 for updating inventory requirements associated with aligning prescriptions. Those of ordinary skill in the art will appreciate that these modules may be implemented in any number of modules, and that their functions need not be divided as indicated in FIG. 1A.

Finally, the prescription alignment back-end systems may include one or more administrator workstations 149. The administrator workstation 149 allows an authorized user to access the various applications running on the central processing systems 140 to alter or adjust the operation of the prescription alignment system 100. For example, a regulatory agency (e.g., a state government) may change its rules regarding dispensing prescriptions, or a third-party payor (e.g., an insurance provider) may change its rules regarding prorating prescription copays. The administrator may then access the central processing systems 140 via the administrator workstation 149 and alter rules active in the customer/prescription eligibility module 142, to reflect the changes in regulatory or third-party payor rules.

For purposes of implementing the prescription alignment system 100, the primary point of contact with the customer is through the pharmacy. As used herein, the term "customer" may be, by way of example, a patient (i.e., the person named on the prescription), a guardian (e.g., the parent of a child named on the prescription), a care-giver (e.g., an in-home nurse who picks up prescriptions for one or more patients), etc. While term "customer" is used interchangeably with the term "patient," in this specification, the term "customer" is used primarily so as to avoid confusion. Thus, a customer may be a patient (as where a person picks up his/her own prescriptions), but a customer may also be, by way of example, a parent picking up a prescription for a child, a husband picking up a prescription for his wife, a home-care nurse picking up a prescription for one or more patients, a care facility director picking up prescriptions for one or more patients, etc. Also, as mentioned above, the pharmacy may be any of the channels through which the entity implementing the prescription alignment system 100 serves its pharmacy customers. Thus, the pharmacy may be a retail drug store 112 in the customer's neighborhood (or any other drug store in a drug store chain), an on-line pharmacy 114, a mail-order pharmacy 116, or a specialty pharmacy 118 affiliated with the entity implementing the prescription alignment system 100. Whichever channel the customer chooses, the customer must typically interact with a pharmacist or other pharmacy staff (hereafter simply "the pharmacist") in order to have his or her prescriptions filled. The pharmacist filling the prescription will have access to one of the pharmacy workstations 129 or client terminal devices 128 and may invoke the prescription alignment system 100 when he or she fills the customer's prescription. Alternatively, the prescription alignment system 100 may be invoked automatically for each new prescription entered (e.g., by reminding the pharmacist to ask whether the customer would like to align his or her prescriptions) or by a broader system, such as a medication management system.

Generally, a prescription has associated with it a plurality of data. The plurality of data may include, but is not limited to: a date the prescription was written; a doctor who prescribed the medication; a name of the medication prescribed; an indication of whether a generic may be substituted for the prescribed medication; a number of days of medication to be dispensed (also referred to herein as a "prescribed day supply" or a "pre-alignment day supply"); a number of refills prescribed; a first date on which the prescription was filled; a date on which the prescription was most recently filled (also referred to herein as a "last fill date"); and a store at which it was most recently filled. The alignment system 100, using this information, determines an alignment date (or otherwise receives an alignment date selection), on which the plurality of selected prescriptions will each be filled with a post-alignment day supply (e.g., each prescription being dispensed with a 60-day supply, a 90-day supply, etc). Aligning the plurality of selected prescriptions may require adjusting the day supply for one fill for each of one or more of the selected prescriptions, for example, by dispensing more of the medication ("overfilling") or less of the medication ("underfilling") such that the customer's supply of a first medication runs out at the same time as the supply of a second medication. An underfilled prescription is referred to herein as a reduced fill. Each reduced fill has an associated reduced-fill date, on which the reduced fill is dispensed, and an associated reduced-fill day supply, indicating the number of days of medication dispensed.

A customer profile is created for every customer who purchases his/her medication at the pharmacy. The customer profile is a record that stores important information about the customer and the various pharmacy services that have been invoked on behalf of the customer. The customer profile may retrieve basic customer information, such as name, address, phone number, insurance group number, prescription history, etc., from the legacy systems data stores 148. The prescription history may include, but is not limited to, data such as: a list of the customer's prescriptions, and for each, the last fill date, the pre-alignment day supply, a number of refills remaining, etc. Additional data relating specifically to the customer's prescription alignment program may be stored in the prescription alignment database 146. The additional data may include, but is not limited to, data including: the plurality of prescriptions selected for alignment; one or more selected alignment dates; the post-alignment day supply for each prescription; which of the selected prescriptions requires a reduced fill; a reduced-fill date for any required reduced fill; a reduced-fill day supply for any required reduced fill; and a reduced-fill cost for any required reduced fill.

Figure 2:
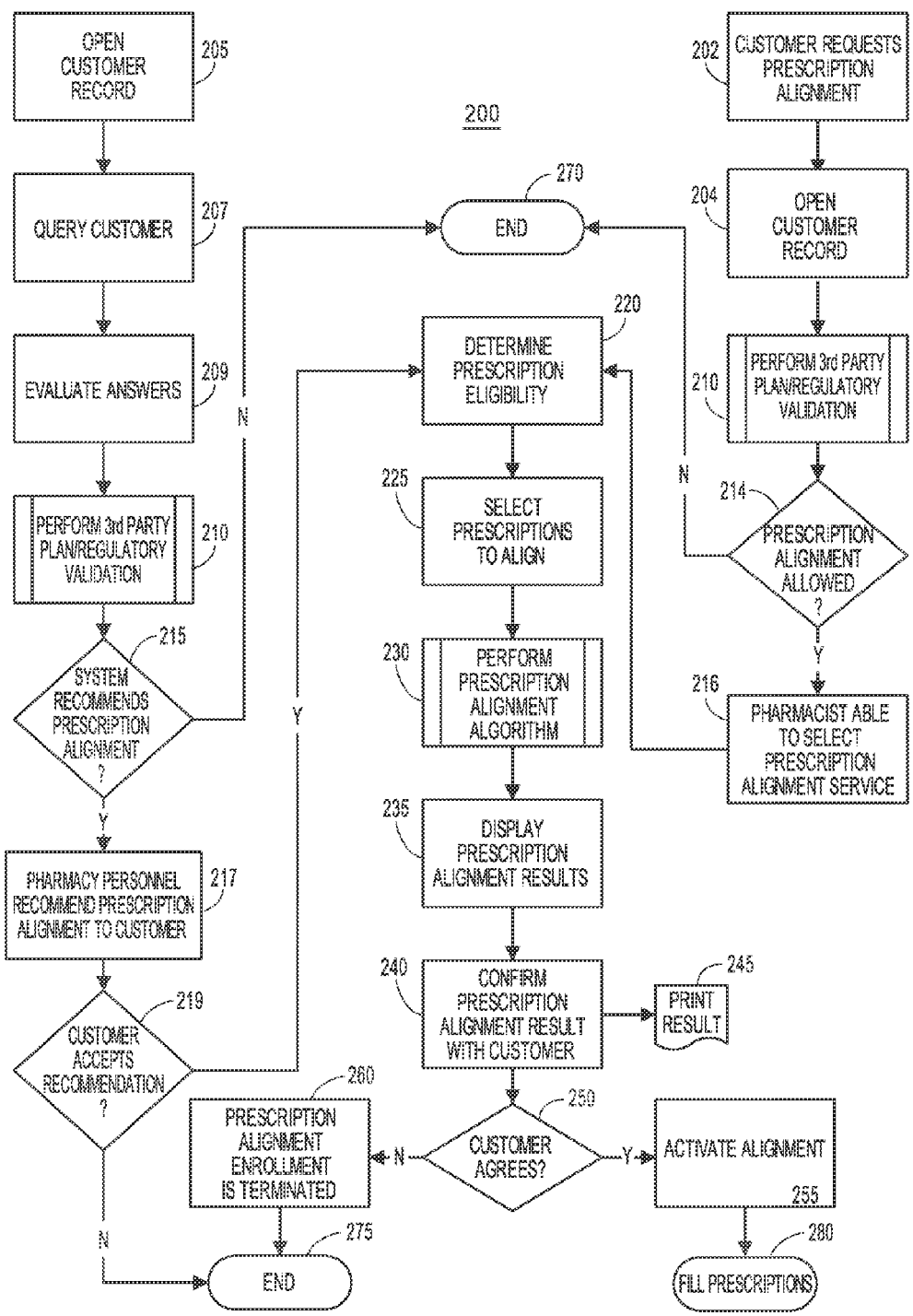
FIG. 2-5 illustrate an exemplary process for aligning a plurality of prescriptions in accordance with the described embodiments.

FIG. 2 shows an exemplary process 200 for activating prescription alignment for a customer. The exemplary process 200 allows initiation of prescription alignment in at least two different ways. First, a customer could request that prescription alignment be implemented. The system may receive such a customer request in a step 202 via any of the various front-end components 102. For example, a customer may walk into a retail pharmacy 112 and make the request to a pharmacist who would enter the request into the system via the client device terminal 128 or the workstation 129. Alternatively, a customer could use a kiosk 120 or an Internet interface terminal 124 (e.g., the customer's home computer connected to the Internet) to enter a request for prescription alignment. Likewise, the customer request for prescription alignment may be received by the system via a call center terminal 122, or may be entered by personnel at a specialty pharmacy 118 or a mail order pharmacy 116, upon receiving the customer request.

After receiving, in step 202, the customer request to implement prescription alignment, the system opens the appropriate customer record in step 204 and performs a third-party-plan and regulatory validation step 210 to determine whether any rules of the customer's third party plan, if there is one, or the applicable regulatory agency would prevent prescription alignment. The system then evaluates the output of step 210 in a step 214. If prescription alignment is not prohibited, the pharmacist is allowed to select prescription alignment in step 216, and the prescription alignment process continues. If prescription alignment is prohibited, on the other hand, the process ends in step 270.

Alternatively, and by way of example and not limitation, the pharmacist may recommend prescription alignment. This may be done of the pharmacist's own accord, may be suggested to the pharmacist by a customer service software package, such as a prescription compliance advisory system, may be suggested by the prescription alignment software, or may be suggested by any other system wherein a customer record is evaluated to determine which of a plurality of available services may be beneficial or applicable to a customer. For example, in the case of a prescription compliance advisory system, a customer may bring a new prescription into a retail pharmacy 112, to have the new prescription filled. Upon receiving the new prescription, the pharmacist opens the appropriate customer record in a step 205. In a step 207, the pharmacist may query the customer according to a pre-determined question set, to determine what services may benefit the customer. Upon evaluating the customer's answers in step 209, and determining that the customer could benefit from prescription alignment, the system may perform the third-party-plan and regulatory validation step 210 to determine whether any rules of the customer's third party plan, if there is one, or the applicable regulatory body would prevent prescription alignment. If prescription alignment would benefit the customer, and the alignment is not determined, in step 210, to be prohibited, the system decides whether to recommend prescription alignment to the customer in step 215. If alignment is recommended, the pharmacist recommends alignment to the customer in step 217. If the system does not recommend prescription alignment (e.g., because rules of one of the third-party-plan or the applicable regulatory body would prevent alignment) or the customer does not accept the pharmacist's recommendation in step 219, the prescription alignment process 200 ends in step 275. If, on the other hand, the customer does accept the pharmacist's recommendation in step 219, the prescription alignment process continues.

Regardless of whether prescription alignment is initiated by a customer request or a pharmacist recommendation, prescription alignment continues by determining, in step 220, which of the plurality of prescriptions associated with the retrieved customer are eligible for prescription alignment. Eligibility may be determined by a number of factors, and may be different depending upon the sophistication of the prescription alignment system 100, as well as the preferences of the pharmacy implementing the prescription alignment system 100, the regulations of the relevant regulatory agency, and the third-party payor associated with the customer. Factors that may determine eligibility include, by way of example and not limitation: (1) the form of the medication (e.g., pill/capsule, liquid, inhalant, etc.); (2) the type of medication (e.g., antihistamine, narcotic, steroid, etc.); (3) whether the prescription is considered a maintenance medication (i.e., one that is taken on a regular schedule over a long period of time) (e.g., blood pressure medications, antihistamines, beta-blockers, blood thinning agents, etc.); (4) how often the medication is taken (e.g., daily, weekly, monthly, etc.); and (5) the type of packaging (e.g., unit-of-use, unit-dose, etc.) in which the medication is sold. Birth control pills, for instance, are typically sold in a package containing a 28-day supply (a unit-of-use package), which may prevent them from being eligible. In one embodiment of the prescription alignment system, a prescription dispensed in a unit-of-use package, for example, may be eligible for prescription alignment. In such an embodiment, the system may allow alignment of a plurality of prescriptions including a prescription dispensed in a unit-of-use package. As those of ordinary skill in the art can appreciate, the refill date of the unit-of-use package could serve as the preferred alignment date of the plurality of prescriptions.

Eligibility of each prescription may be, but need not necessarily be, determined by the prescription alignment system 100 (i.e., by a computer device). In one embodiment, a database 146 or 148 maintains an indication, for each available medication, of which medications are eligible for prescription alignment and which are not. Alternatively, a database 146 or 148 may maintain an array of medication properties (e.g., type of medication, form of dispensation, whether the medication is a maintenance drug, etc.) and the central processing system 140 (or legacy system 147) may compare the properties for each medication to a list of eligibility requirements for a particular customer or third-party plan. Additionally, an override feature may exist to allow a pharmacist to override or ignore a determination that a given prescription is not eligible for prescription alignment.

Following the determination of eligibility, in step 220, the alignment process continues by selecting, in step 225, a plurality of prescriptions to align. The selected prescriptions are, in the exemplary embodiment, selected from the eligible prescriptions associated with a single customer record. Alternatively, the selected prescriptions may be determined based upon each medication's status as a brand name medication or a generic medication. The prescriptions may be last-filled at different locations within a chain of retail pharmacies, at the same location other than the current location in a chain of retail pharmacies, or at the location implementing the alignment procedure or at any combination of these. Additionally, the pharmacy may implement procedures for transferring prescriptions associated with a customer from a different pharmacy (i.e., one not part of the same chain or network) to the pharmacy implementing the prescription alignment procedure.

While the first exemplary embodiment contemplates alignment of a plurality of prescriptions associated with a single customer, those of ordinary skill in the art will appreciate that a number of alternative alignment possibilities exist including, but not limited to, aligning a plurality of prescriptions associated with customers residing in a single residence (e.g., a family, roommates, etc.), customers under the care of a single facility (e.g., a nursing home, hospice, etc.), or customers under the care of a single home-care professional. Thus, in such a system, a plurality of customer records may be retrieved, eligibility may be determined by multiple third-party payor rules and regulatory rules, and the plurality of prescriptions to align chosen from multiple customer records.

Once the plurality of prescriptions to be aligned is selected in step 225, prescription alignment proceeds with the alignment algorithm performed in step 230. The results of step 230 are displayed for the pharmacist in a step 235. After reviewing the results displayed in step 235, the pharmacist (for a customer in a retail pharmacy) may review the results with the customer in a step 240 and may further print the results in a step 245 to facilitate this process. If the customer accepts, in step 250, the results of the prescription alignment algorithm 230, prescription alignment is activated in a step 255, and prescriptions are filled in a step 270, according to the results of the prescription alignment algorithm 230. If, on the other hand, the customer does not accept the prescription alignment algorithm results in step 250, enrollment in the prescription alignment program is terminated in step 260, and the process ends in step 275.

While in the exemplary embodiment of the process 200, the steps described above occur in a set order, it should be noted that each of the steps need not be performed in the order described above. For example, step 210, evaluating the rules of the customer's third party plan and the applicable regulatory body, could be performed after the customer accepts a recommendation from the pharmacist to attempt prescription alignment in step 219, as part of the prescription alignment algorithm 230, or even after the customer has accepted the results of the alignment algorithm and as part of the prescription alignment activation step 255. It should also be noted that additional steps may be performed without destroying the utility of the process 200. For instance, the customer's list of prescriptions may be evaluated, as described below, to determine how many, and which, of the prescriptions may be eligible for prescription alignment.

Figure 3:
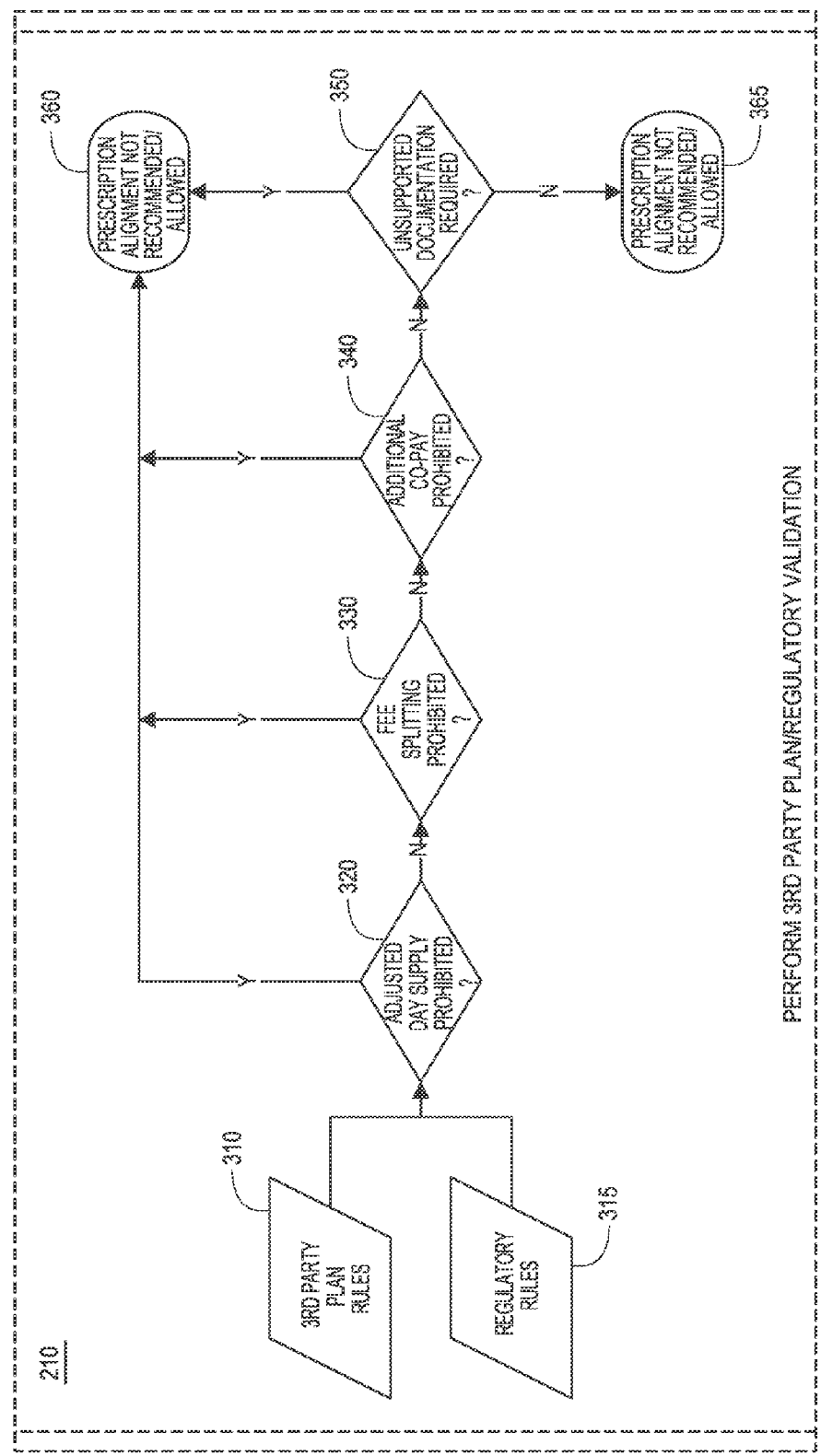

Referring now to FIG. 3, the third-party plan and regulatory validation is performed as step 210 of the process 200 shown in FIG. 2. The validation process 210 retrieves the relevant third-party plan or plans in step 310 and the relevant regulatory rules in step 315. For example, the relevant third-party plan or plans could include an insurance plan or plans associated with the customer for whom alignment is being evaluated, Medicare, Medicaid, etc. The relevant regulatory rules could include, for example, any state, federal, or local rules that apply to the sale or dispensation of prescription medication.

Figure 4:
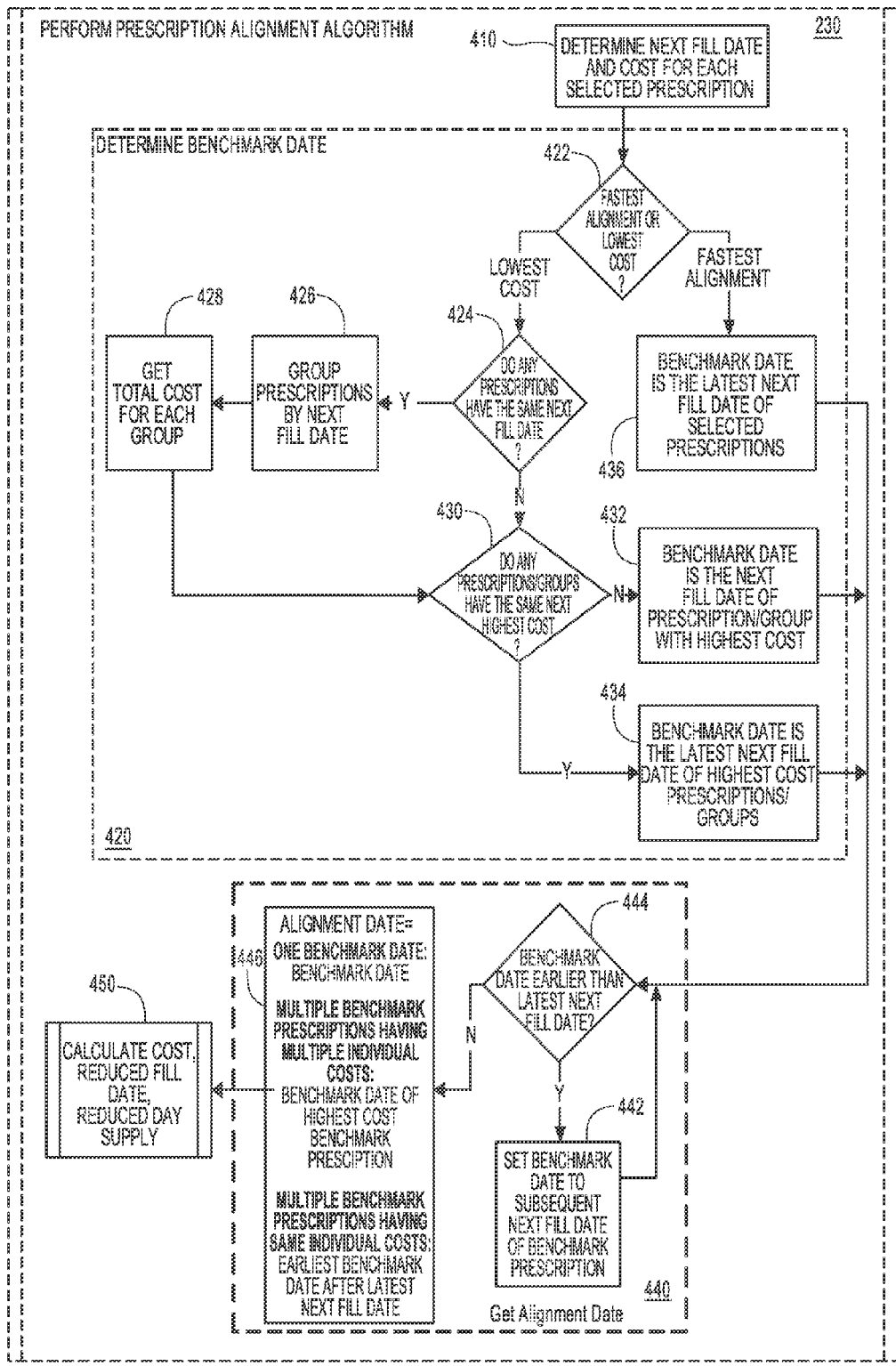
Figure 5:
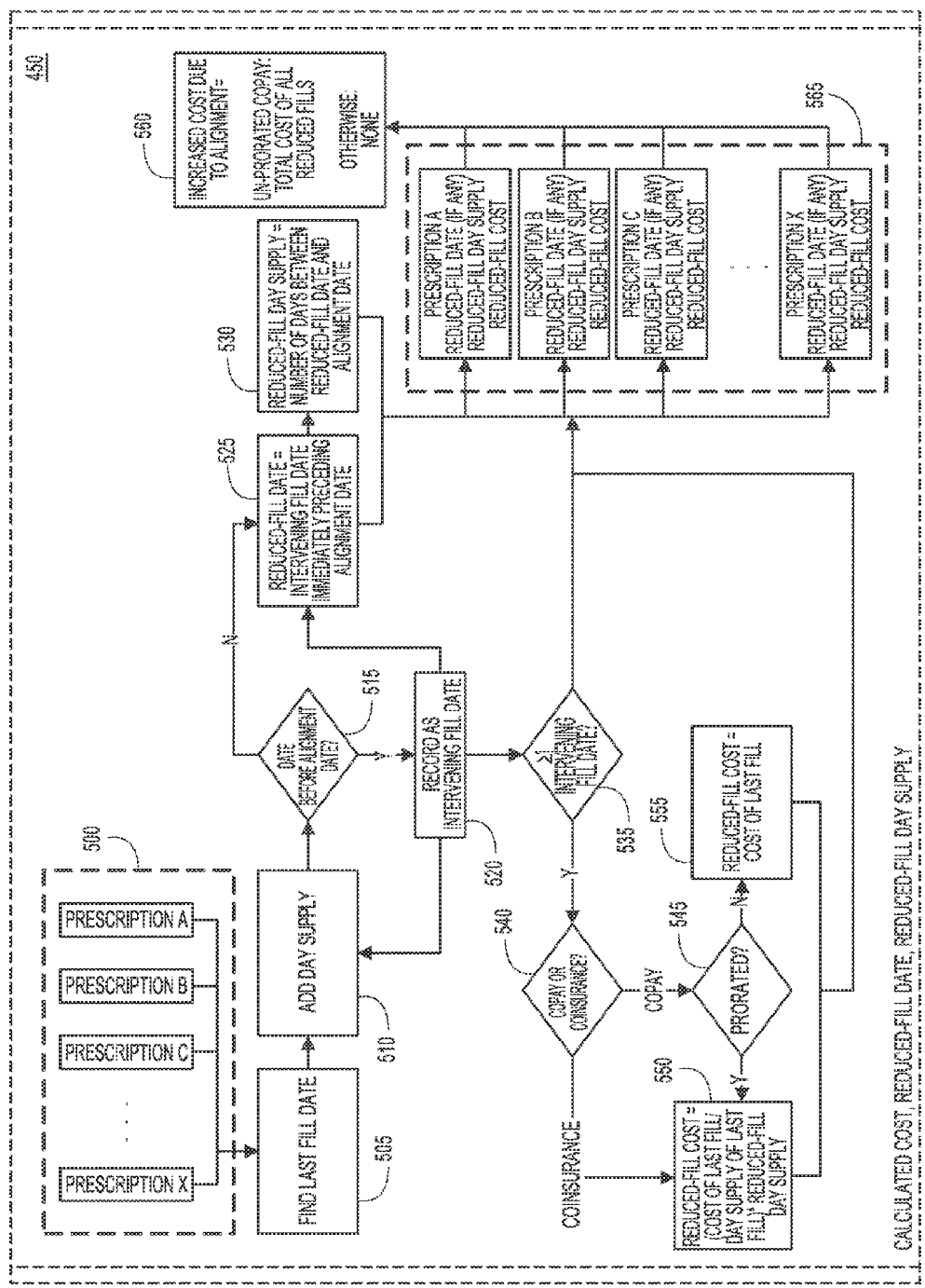

As will be seen with reference to FIGS. 4 and 5, prescription alignment may require a number of pharmacy practices that could be regulated by a customer's third-party plan (e.g., an insurance provider) or by regulations (e.g., state law). For example, prescription alignment may require adjusting the quantity of a medication supplied (also referred to as the "day supply"), as described above, by overfilling or underfilling the prescription. If, for example, a customer's insurance company or state law prohibits the pharmacist from dispensing an adjusted day supply, prescription alignment cannot be achieved without getting a new prescription for any medication that would otherwise require an adjusted day supply.

Another practice that may be required for prescription alignment is fee splitting. As is known by those of ordinary skill in the art, a number of fees and costs may be associated with the sale of a prescription medication. Such fees and costs may include, but are not limited to: the cost of the medication to the pharmacy, dispensing fees charged to the customer or a third-party payor (e.g., the customer's insurance company), the medication cost paid to the pharmacy by the third-party payor (e.g., the average wholesale price), and the medication cost paid to the pharmacy by the customer (e.g., a co-payment (a "copay"), a co-insurance amount, etc.). Unless otherwise specified, any discussion of cost within this specification is the cost to the customer, such as a copay or a co-insurance amount. Fee splitting, as the term is used herein, refers to charging of the dispensing fee to a third-party payor for an underfill of the medication. If a customer's insurance plan, for example, prohibits fee splitting, an underfill of the prescribed medication may be prohibited by extension, unless the pharmacy waives the dispensing fee, the customer pays the dispensing fee, or unless prescription alignment can be achieved by an dispensing an overfill (assuming that overfilling a prescription is not prohibited by the rules). Similarly, if a customer is responsible for a copay, the third-party payor rules or the regulatory rules may prohibit charging the customer the extra copay required for the underfill dispensed to achieve alignment. If such a prohibition is in place, alignment may not be possible unless the insurance company is circumvented altogether (i.e., the customer pays for the drug entirely out of pocket).

Another alternative is that one or more of the costs associated with the prescription alignment process including, but not limited to, additional dispensing fees, additional copays, or costs of medication associated with a reduced fill, is reimbursed. For example, if a customer is required to pay an additional copay as a result of a reduced fill required to implement prescription alignment, the cost could be reimbursed by a third party. The third party may be a drug manufacturer hoping to improve, via prescription alignment, the percentage of customers using the medication as it is prescribed. Alternatively, the third party may be a drug distributor seeking an exclusive contract with the pharmacy implementing the prescription alignment system. Another alternative is that the third party may be a drug retailer (such as the pharmacy itself) seeking to expand its customer base by offering to absorb the costs of prescription alignment and to better serve its customers. Yet another alternative is that the third party may be an insurance company seeking to increase medication compliance (and therefore the health) of the customer.

Alternatively, some third-party plans may allow the pharmacy to prorate one or more of the dispensing fee, the administration fee, the copay, or the cost paid by the third-party plan according to the proportion of the medication dispensed for the underfill. For example, a customer with a prescription for a 30-day supply of a medication may be required by his or her third-party plan (e.g., an insurance policy) to pay a $30 copay for the medication, and the pharmacy may charge a $5 dispensing fee to the third-party payor (in addition to the cost of the medication). If prescription alignment requires a reduced fill of a 15-day supply, the pharmacy may charge the customer $15 (half of the copay for half of the medication) and the third-party payor $2.50 (half of the dispensing fee for half of the medication).

The practices described above may be necessary for prescription alignment, but may be prohibited by the rules of a third-party payor or a regulatory body. There may also be practices required by a third-party payor or a regulatory agency that are unsupported by the procedures implemented by a particular pharmacy. For example, state regulations may require that the pharmacy document an underfill. If the prescription alignment system is not set up to provide that documentation, the requirement for the documentation will prevent implementation of prescription alignment for the customer.

To these ends, the present embodiment evaluates each set of rules to determine whether the rules prohibit the pharmacist from adjusting the day supply of medication dispensed 320, whether the rules prohibit fee splitting 330, whether the rules prohibit an additional copay 340 and whether any set of rules being evaluated requires documentation that the system does not support 350. If the answer to any the questions enumerated in 320-350 is positive, prescription alignment is not recommended (in the case of the pharmacist recommending prescription alignment) or allowed (in the case where the customer requests prescription alignment).

Those of ordinary skill in the art will appreciate that the situations described in the paragraphs above are exemplary of the requirements and prohibitions that could potentially prohibit implementation of prescription alignment, and such requirements and prohibitions are not limited to those illustrated above or in FIG. 3. By way of example, and not limitation, other prohibitions, requirements or limitations may include such things as whether the customer can afford to (or is willing to) pay a required additional copay, whether the customer's insurance or a relevant regulatory body will allow the customer to pay the dispensing fee or the medication cost in cash (i.e., circumvent insurance altogether), and whether the prescribing physician requires documentation of changes to a prescription. Accordingly, the validation process 210 may, in alternate embodiments, include rules or other data emanating from the patient (e.g., acquired during step 207) or the prescription for a particular medication (i.e., stored as part of the prescription data in a database 146 or 148), in addition to the third-party plan rules and regulatory rules.

FIG. 4 illustrates in more detail the prescription alignment algorithm performed in step 230. In general, the exemplary prescription alignment process illustrated in FIG. 4 adjusts the day supply of one or more of the prescriptions selected to be aligned such that on the selected alignment date, each of the selected plurality of prescriptions requires a refill. By refilling each of the aligned prescriptions with the same day supply (a "post-alignment" day supply) on the alignment date (and thereafter), the plurality of aligned prescriptions will remain aligned, requiring a refill on the same date (assuming that the customer uses the prescription as directed).

The alignment algorithm 230 comprises four basic steps. In step 410, a next fill date and a cost are computed for each selected prescription. Next, a benchmark date is determined in step 420. Having determined a benchmark date, an alignment date is determined in step 440. For the determined alignment date, step 450 calculates costs, reduced-fill dates, and reduced-fill day supplies.

As described above, the alignment algorithm starts by determining the next fill date and cost, in step 410, for each of the prescriptions selected for alignment. By way of example, and with reference to FIG. 6, a prescription 601 last filled with a 30-day supply on August 1, would have a next fill date of August 31. A prescription 604 last filled with a 28-day supply on July 31, would have a next fill date of August 28. For the prescriptions 601-605 shown in FIG. 6, the next fill dates for each of the prescriptions as of August 8 would be:

A: August 31
B: August 19
C: August 28
D: August 28
E: October 5

Once the next fill dates for each of the selected prescriptions 601-605 has been determined, a benchmark date (and corresponding benchmark prescription) may be determined. A step 422 determines what benchmark date (and alignment date) the system will calculate. As one possibility, the system may calculate a benchmark date (and an alignment date) corresponding to the fastest alignment of the prescriptions, such that the prescriptions are aligned in the shortest possible time period. Alternatively, the system may calculate a benchmark date (and an alignment date) corresponding to a lowest-cost alignment of the prescriptions, in which the additional cost due to alignment (e.g., additional copays) is minimized. Additionally, the system may calculate a benchmark date (and alignment date) based upon the status of the medication as a brand name medication or a generic medication. To calculate the benchmark date for the fastest alignment of the selected prescriptions, the benchmark date is simply the latest of the next fill dates—October 5 in the example illustrated in FIG. 6.

Calculating the benchmark date for the lowest-cost alignment of the selected prescriptions 601-605 is more involved, however. To calculate the benchmark date for the lowest-cost alignment, a step 424 first determines whether any of the selected prescriptions have the same next fill date. If any of the selected prescriptions have the same next fill date, the prescriptions are grouped by their next fill dates in step 426. Thus, with reference to FIG. 6, if the current date is August 8, the results of step 426 would be:

Group A: August 31
Group B: August 19
Group C-D: August 28
Group E: October 5

Having grouped the prescriptions by each prescription's next fill date in step 426, step 428 determines the total cost for each of the prescription groups. For example, if the customer pays a $10 copay for any generic prescription and a $20 copay for any brand name prescription, the total costs for the four groups may be:

Group A (Generic): $10
Group B (Brand Name): $20
Group C-D (Both Generic): $20
Group E (Generic): $10

If, in step 424, none of the selected prescriptions has the same next fill date as another, the exemplary algorithm proceeds directly to step 430. Of course, while it is efficient to skip steps 426 and 428 in the event that the selected prescriptions each have different next fill dates, it will be apparent to those of ordinary skill in the art that the results in such a case would be the same with those steps as without them (i.e., five groups each having only a single prescription in the group).

Step 430 determines whether any of the groups (or prescriptions, if none have the same next fill date) have the same highest cost. If, the highest cost is $20, as it is in the current example, then groups B and C-D each have the same highest cost—$20. Thus, step 430 would proceed to step 434, and the benchmark date is the latest next fill date of the highest cost groups (or prescriptions, if more than one prescription has the same highest cost)—August 28 in the example illustrated in FIG. 6 and described above (making prescriptions C and D the benchmark prescriptions). If, on the other hand, none of the groups (or prescriptions, if none have the same next fill date) have the same highest cost, the algorithm proceeds to step 432, and the benchmark date is the next fill date of the group or prescription with the highest cost.

Having determined a benchmark date in step 420, the algorithm proceeds to determine a corresponding alignment date in step 440. A step 444 first determines whether the benchmark date is earlier than the latest next fill date. If the benchmark date is not earlier (i.e., the same as or later) than the latest next fill date, the benchmark date is set as the alignment date in step 446. On the other hand, if the benchmark date is before the latest next fill date, the benchmark date is updated in step 442 and step 444 is repeated. The benchmark date is updated in step 442 by finding the subsequent next fill date for the benchmark prescription (i.e., adding the day supply for the benchmark prescription to the benchmark date).

Figure 6:
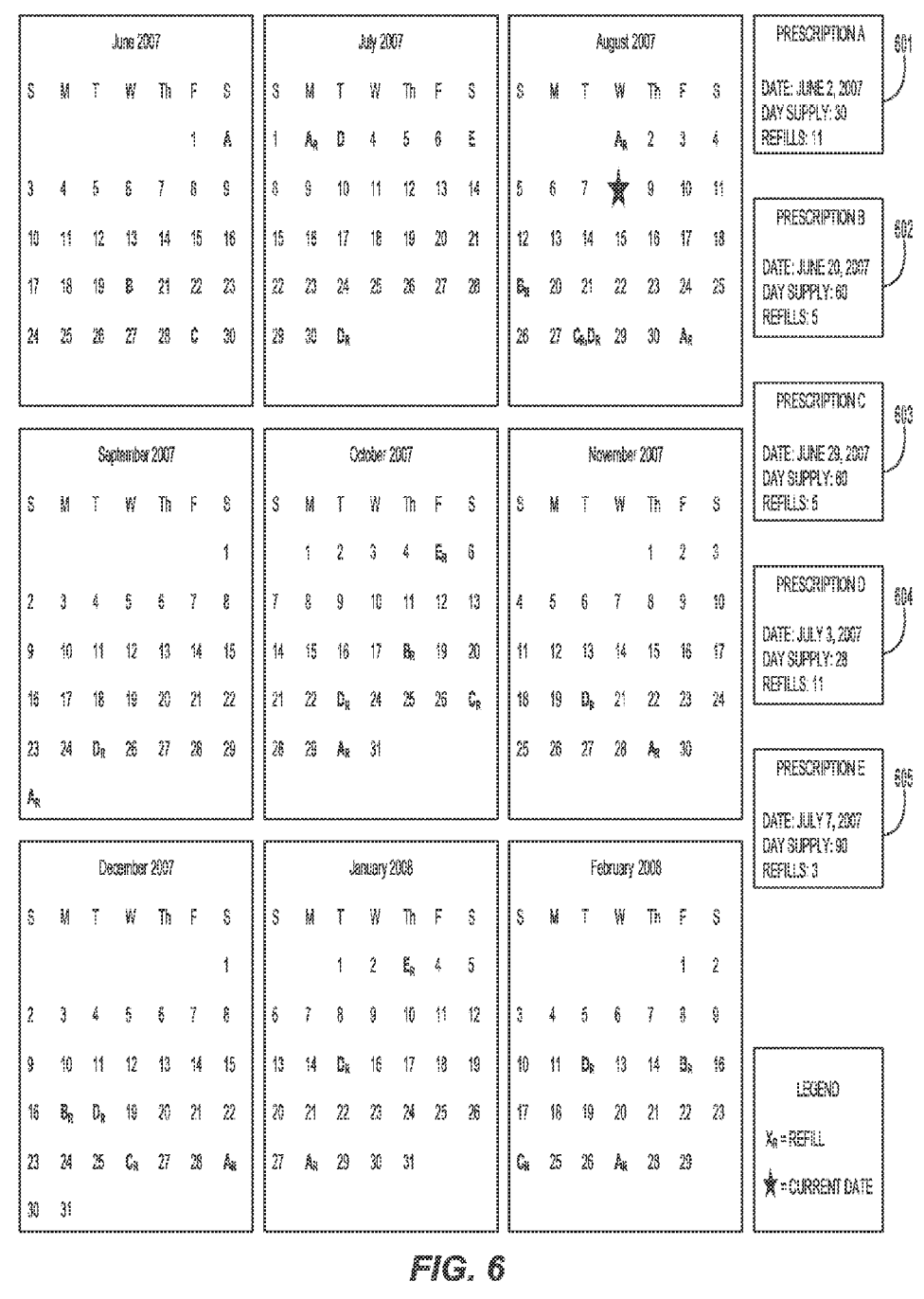

In the example illustrated in FIG. 6 and discussed above, the benchmark date (August 28) is earlier than the latest next fill date (October 5). Thus, the algorithm would proceed from step 444 to step 442 and the benchmark date would be updated by adding the day supply for the benchmark prescription to the benchmark date. In the illustrative case above, there are two benchmark prescriptions (C and D). Finding the subsequent next fill dates for each yields a subsequent next fill date for prescription C of October 27 (August 28 plus 60 days) and a subsequent next fill date for prescription D of September 25 (August 28 plus 28 days). Control would then return to step 444, and the two new benchmark dates —September 25 and October 27 —would each be compared to the latest next fill date (October 5). October 27 is clearly not earlier than October 5, so October 27 is a benchmark date. September 25, on the other hand, is earlier than October 5, so for that prescription, control is once again passed to step 442. The next output of step 442 is October 23 (September 25 plus 28 days).

Once again comparing the subsequent next fill date for prescription D (October 23) to the latest next fill date (October 5) in step 444, both prescriptions C and D now have benchmark dates later than the latest next fill date, and control passes to step 446. In step 446, the alignment date is the benchmark date of the benchmark prescription having the highest individual cost or, where each of the benchmark prescriptions costs the same, the earliest of the benchmark dates after the latest next fill date. In the example illustrated in FIG. 6 and described above, both of the benchmark prescriptions (C and D) have the same cost (both are generic and cost $10). Thus, the earliest benchmark date (after the latest next fill date) is the alignment date (October 23).

While the system 100 may calculate an alignment date associated with either or both of the lowest cost alignment option or the quickest alignment option, the user (or customer) may likewise opt to choose an alignment date that does not correspond to either. Where this is the case, the alignment algorithm 230 proceeds in the same way, using the custom alignment date instead of the alignment date determined via the determination of a benchmark date (step 420) and the determination of an alignment date (step 440) from the benchmark date.

While the presently preferred embodiment of the prescription alignment system described herein aligns a plurality of prescriptions to a single selected alignment date, those of ordinary skill in the art will appreciate that the system could also align a plurality of selected prescriptions to a plurality of selected alignment dates. Any number of reasons and corresponding alignment schemes may present themselves. For example, a customer with 10 prescriptions may wish to align half of the prescriptions to one date and half of the prescriptions to a second date to make the copay more manageable. An alternate embodiment of the currently disclosed prescription alignment system may divide the 10 prescriptions between two or more alignment dates, evenly distributing the total copay among the plurality of selected alignment dates.

As described above, having selected an alignment date in step 440, control proceeds to step 450, in which the prescription alignment system calculates an alignment cost, determines the dates of any reduced fills (underfills), and calculates the day supply for each required reduced fill. Referring to FIG. 5, step 450 starts with the plurality of prescriptions selected for alignment 500. For each prescription, the system retrieves the last fill date in step 505, and adds the day supply of the last fill to the last fill date in step 510. A step 515 determines whether the new date is before the alignment date. If the new date is before the alignment date, the date is recorded as an intervening fill date in step 520 and control returns to step 510. The day supply is added again to the determined intervening fill date, and control again returns to step 515 to determine whether the new date is before the alignment date. The algorithm proceeds in this manner until the date determined by step 510 is equal to or later than the selected alignment date.

Figure 7:
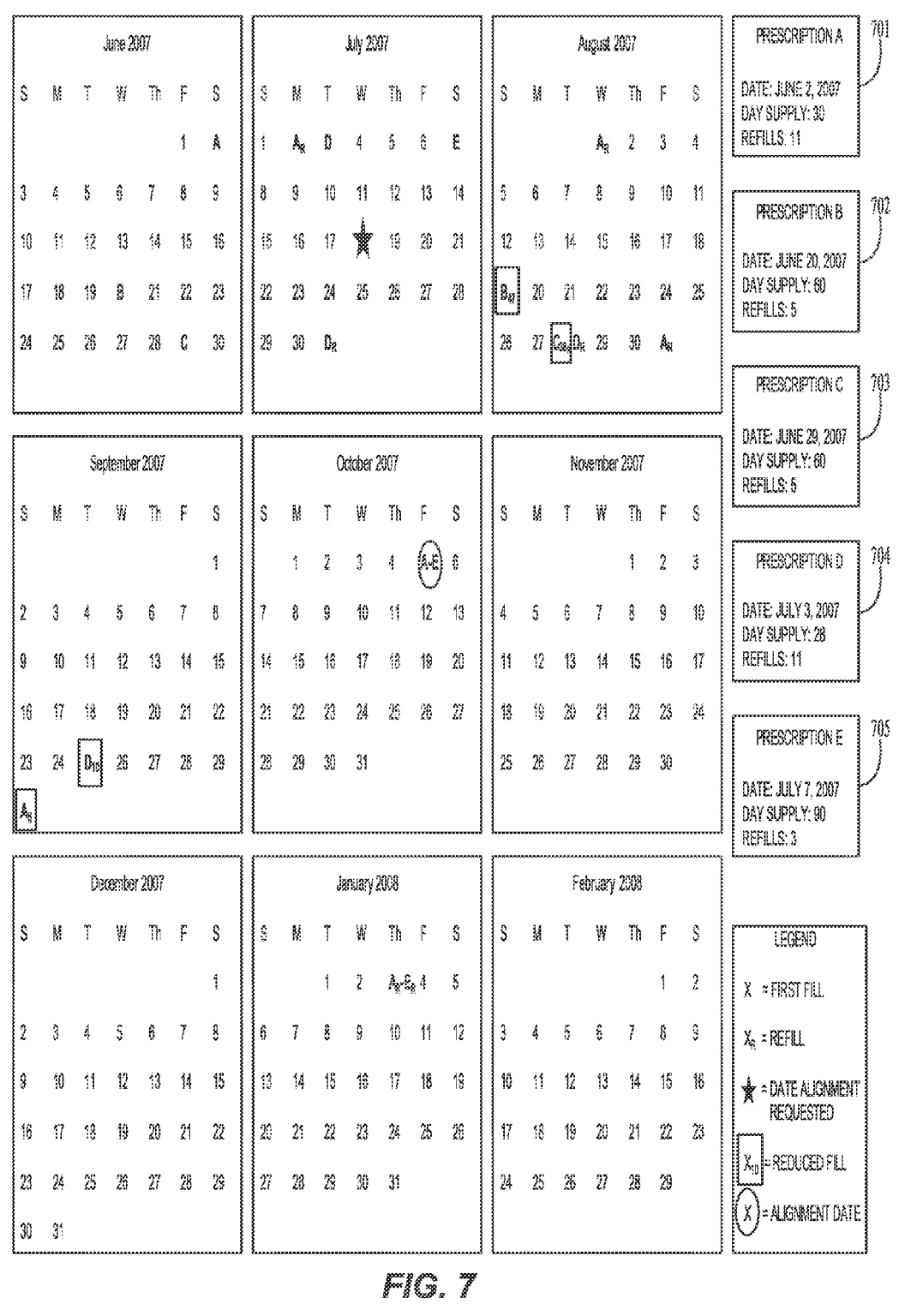

For example, and with reference to FIG. 7, a plurality of prescriptions 701-705 has a selected alignment date of October 5, corresponding to the fastest alignment date. If a customer requested alignment on July 18, steps 505-520 would yield the following sets of intervening fill dates for each prescription:

| Prescription A | Prescription B | Prescription C | Prescription D | Prescription E |
|---|---|---|---|---|
| August 1 August 31 September 30 | August 19 | August 28 | July 31 August 28 September 25 | None |

Having determined in step 515 that the date from step 510 is on or after the selected alignment date, a step 525 sets the intervening fill date (if one exists) immediately preceding the selected alignment date as the reduced-fill date for the prescription. A step 530 then determines the number of days between the reduced-fill date and the selected alignment date, and sets that as the reduced-fill day supply for the prescription. As shown in FIG. 7, the reduced-fill dates and reduced-fill day supplies for each of the selected prescriptions would be:

| Prescription | Reduced-Fill Date | Reduced-Fill Day Supply |
|---|---|---|
| A | September 30 | 5 |
| B | August 19 | 47 |
| C | August 28 | 38 |
| D | September 25 | 10 |
| E | None | N/A |

For each of the selected prescription 500, a step 535 determines whether there is at least one intervening fill date. If there is at least one intervening fill date for a prescription, the system determines, in a step 540, whether the customer's insurance plan (or other third-party plan) requires a copay or a coinsurance payment. If the customer's plan requires a coinsurance payment, the system determines the cost of the reduced-fill in step 550, by dividing the cost of the last fill by the day supply of the last fill—to find the cost per day of the prescription—and then multiplies that by the reduced-fill day supply determined in step 530. Alternatively, if the customer's plan requires a copay, step 540 passes control to step 545, in which the system determines whether the customer's plan allows the pharmacy to prorate the copay. If the customer's plan allows a prorated copay, control passes to step 550, and proceeds as described above. If the customer's plan does not allow a prorated copay, the reduced-fill cost is determined in step 555, and the cost of the reduced-fill is the same as the cost of the last fill.

Having completed the applicable steps 505-555 for each of the selected prescriptions 500, and stored the reduced-fill date (if a reduced fill is required), the reduced-fill day supply, and the reduced-fill cost for each of the selected prescriptions 565, the system, in a step 560 may determine the total cost of the reduced fills, by summing the reduced-fill costs of each of the prescriptions 565. The system may also determine the increased cost due to alignment. For a customer who makes a coinsurance payment, or a customer with a plan allowing a prorated copay, there is no increased cost due to the alignment procedure. (A customer receiving a 15-day supply instead of a 30-day supply only pays half the copay.) For a customer with a plan that does not allow a prorated copay, the increased cost due to alignment is the total cost of any required reduced fills.

FIGS. 8 and 9 depict an exemplary embodiment of a user-interface 800-900 for entering and displaying information related to a prescription alignment system 100. A first page or screen 800 displays a list of active prescriptions and related information associated with the customer. The first page 800 includes an indication 802 of the customer name and an indication 804 of the current date. A plurality of column headings 806a-806f indicate what additional data is displayed on the page. In one exemplary embodiment, illustrated in FIG. 8, the column headings include a prescription number 806a, a store number at which the prescription was last filled 806b, a medication name 806c, a last fill date 806d, a prescribed (i.e., pre-alignment) day supply 806e and a number of refills remaining 806f. Below the column headings 806a-806f, the user interface displays the associated data for a plurality of prescriptions in tabular format, with data for each prescription associated with a single row of the table. For example, a plurality of prescription numbers 820 is displayed below the prescription number heading 806a and a plurality of store numbers 825 is displayed below the store number heading 806b. In a similar manner, a plurality of medications 830 is displayed below the medication name heading 806c, a plurality of last-fill dates 840 is displayed below the last fill date column heading 806d, a plurality of day supplies 850 is displayed below the day supply column heading 806e and a plurality of refills remaining 860 is displayed below the refills remaining column heading 806f.

Additionally, the first page 800 of the user-interface 800-900 includes a plurality of check boxes 810 and 815, with one check box corresponding with each displayed prescription. Using these check boxes, a pharmacist or other user may select the prescriptions that should be aligned during the alignment procedure. As indicated in FIG. 8, prescriptions that are ineligible for prescription alignment may be indicated by an inactive (e.g., grayed-out) check box, so that the user may not select the ineligible prescription for alignment. Alternatively, the user-interface may not display (i.e., hide) an ineligible prescription.

An override option 817 may be provided in some embodiments of the user-interface 800-900, to allow a pharmacist to include in the plurality of prescriptions selected for alignment a prescription that the system, for some reason, determined was ineligible. Other embodiments of the user-interface 800-900, such as those intended for direct use by the customer, for example, may not include the override option 817. Selecting the override option 817 may simply make the inactive check box 815 active or, alternatively, it may display a new window requesting or providing additional information prior to allowing the override to take effect.

An additional check box 870 provides a "select all" option 875. The select all option 875, when selected, selects each of the eligible prescriptions 810 (and 815 if the eligibility has been overridden). This provides a fast and efficient way for a user to select all of the eligible prescriptions for prescription alignment.

As illustrated in FIG. 8, the first page 800 may also include one or more buttons, such as a "Continue" button 880 and a "Cancel" button 885, to allow the user further control over the application. An option 890 causes the user-interface to display a printable version of the information displayed on the first page 800, so that the user may easily print the information in an aesthetically pleasing format.

The first page 800 may also include, for an embodiment of a prescription alignment system allowing alignment of prescriptions associated with a plurality of customer records, a means for selecting a plurality of customer records from which to select prescriptions for alignment.

Referring now to FIG. 9, a second page 900 of the user-interface 800-900 provides the user with information related to the alignment of the selected prescriptions. The second page 900 includes an indication 902 of the customer name and an indication 904 of the current date. The second page 900 displays a plurality of column headings 906a-906e and 908a-908d indicative of prescription data displayed on the page. In one exemplary embodiment, illustrated in FIG. 9, the column headings include a first set of headings 906 corresponding to historical prescription information including, for example, the store number at which the prescription was last filled 906a, a medication name 906b, a last fill date 906c, a dispensed quantity (corresponding to a prescribed day supply) 906d, and the prescribed day supply 906e. A second set of headings 908 corresponds to information related to the alignment of the selected prescriptions, and includes columns for next fill date 908a, reduced-fill date 908b, reduced-fill day supply 908c and reduced-fill copay 908d. Below each column heading 906 and 908, the user interface displays the associated data 910-928 for the plurality of selected prescriptions in tabular format, with data for each prescription associated with a single row of the table.

Additional alignment information 930 may also be displayed on the second page 900 of the user-interface 800-900. The additional alignment information 930 may include, but is not limited to, the selected alignment date, the pre-alignment cost (e.g., the cost of the plurality of selected prescriptions over a common time period), the post-alignment cost, the additional cost due to the alignment procedure, and the total day supply of the aligned prescriptions. An indication 938, which may be modified, for example, by means of a pull-down menu, of a default location at which the customer prefers to pick up the plurality of aligned prescriptions may also be included on the second page 900 of the user-interface 800-900.

The second page 900 of the user-interface 800-900 may also include an indication 934 of the post-alignment day supply of the plurality of aligned prescriptions, and options 932 and 936, which allow the user to edit the alignment date and the post-alignment day supply, respectively. Changing the alignment date by selecting the option 932 may cause the user-interface to update the displayed alignment results accordingly. The indication 934 of the post-alignment day supply of the plurality of aligned prescriptions may, in one embodiment, default to the lowest pre-alignment day supply of the selected prescriptions. Where regulations or standard practices limit the dispensation of a medication to a certain day supply, the system may consider the limitation in determining the default post-alignment day supply for the aligned prescriptions. Increasing the post-alignment day supply by selecting the option 936 may cause the system to display a reminder of applicable regulations, including any regulations requiring a newly written prescription (e.g., such as when increasing the day supply of the medication) and any regulations limiting the day supply allowed for a given medication.

As illustrated in FIG. 9, the second page 900 may display alignment results for a single alignment date option, such as the fastest alignment option or the lowest cost alignment option, at a time. Alternatively, the second page 900 may display results for both the fastest alignment option and the lowest cost alignment options simultaneously, to allow the user to compare the alignment results. In an alternate embodiment, such as where a customer selects multiple alignment dates, each of the multiple alignment dates may be indicated, along with the prescriptions selected for alignment to each date. Where the second page 900 defaults to displaying results for a single alignment date option, such as in FIG. 9, the user-interface may have an indication 960 of which results are currently displayed, as well as an option 965 that allows the user to switch to the alternative alignment option. The second page 900 may additionally include instructions or other prose 955 to aid the user in interpreting the displayed information.

The second page 900, as further illustrated FIG. 9, may also include one or more control buttons 940, 945 and 950. For example, a "Confirm" button 940, may allow a user to implement the selected alignment date in the prescription alignment system 100. A "Change Drugs" button 950 may return the user to the first page 800, where the user may edit the prescriptions selected for alignment. A "Cancel" button 950, may discard the alignment data and return the user to a home screen, or may terminate the application entirely. Like the first page 800, the second page 900 may include an option 970 to cause the user-interface to display a printable version of the information displayed on the second page 900, so that the user may easily print the information in an aesthetically pleasing format.

The exemplary user interface 800-900 illustrated in FIGS. 8 and 9 need not comprise precisely two pages or screens. The information displayed may be formatted differently than in the illustrative figures, such that all of the information may be displayed on a single screen. For example, alignment information for the lowest cost alignment option and the fastest alignment option may be displayed side-by-side on the same screen. Alternatively, the information may be displayed in three or more screens, such as, for example, a prescription selection screen, a fastest alignment option screen, and a lowest cost alignment screen. Those of ordinary skill in the art will recognize multiple configurations that may fit the needs of the current system, and the exemplary embodiments illustrated and described above are not intended to limit the scope of the present invention.

Additionally, the user-interface 800-900, and the prescription alignment system 100, may accommodate the addition of prescriptions to a previously-aligned group of prescriptions. Those of ordinary skill in the art will recognize that a variety of methods may exist for adding a new prescription to a previously-aligned group of prescriptions. For example, a new prescription that has not yet been filled may be dispensed as a reduced fill if the refill date for the previously-aligned group of prescriptions is approaching (e.g., dispensing a reduced fill 28-day supply instead of prescribed 30-day supply if the alignment date is 28 days away). Alternatively, the new prescription may be overfilled (if possible) such that a refill is not needed until the refill date for the previously-aligned group of prescriptions. The user-interface 800-900 and system 100 may also accommodate the deletion of prescriptions from an aligned group of prescriptions, such as when a customer no longer requires the medication.

It should be also be apparent that various embodiments of the user-interface 800-900 may be simultaneously operable within the prescription alignment system 100. For example, a pharmacist at a workstation 129 may be presented with one embodiment of the user-interface 800-900 (e.g., one including the override option 817), while a customer using an internet interface terminal 124 may be presented with another embodiment of the user-interface 800-900 (e.g., one that does not include the override option 817).

Likewise, those of ordinary skill in the art will recognize that the exemplary user-interface depicted in FIGS. 8 and 9 may take the form of a web page, transmitted over the network 130 (e.g., the Internet) from the prescription alignment central processing systems 140, as described above with reference to FIG. 1A. Alternatively, the user-interface may be part of a specific software application running on one or more of the client device terminals 128 or the workstations 129. In yet another alternate embodiment, the application may be running on a facility server 126 or the central processing system 140, and transmitted to the client device terminals 128 or the workstations 129 via the network 130.

Once the prescription alignment has been confirmed using the confirm button 940, alignment is activated (see step 255 in FIG. 2). The pharmacy may then fill the prescriptions (see step 270 in FIG. 2) according to the alignment results generated by algorithm 230. Filling the prescriptions according to the alignment results comprises: (1) dispensing, for each selected prescription, the pre-alignment day supply for the prescription on each intervening fill date for the prescription; (2) dispensing, for each selected prescription requiring a reduced fill, the reduced-fill day supply for the prescription on the reduced-fill date for the prescription; (3) dispensing, for each selected prescription, the post-alignment day supply on the alignment date; and (4) dispensing, for each selected prescription, the post-alignment day supply on each refill date following alignment.

Those of ordinary skill in the art will appreciate that various automation techniques may be employed in filling the prescriptions (step 270). In one embodiment employing such techniques, the prescription alignment system may automatically schedule refill dates subsequent to the alignment date, such that no intervention is required by the customer to initiate the refill process. In another embodiment, the prescription alignment system may automate each of the required fills associated with the alignment results, including filling each prescription on any intermediate fill dates for the prescription, filling each prescription on any reduced-fill dates for the prescription, and filling each prescription on the alignment date. In yet another alternate embodiment, manual intervention may be optionally prevented so as to prevent the customer or pharmacist from scheduling a refill date that does not follow the alignment schedule determined by the algorithm 230. In a further embodiment, the prescription alignment system may, before a scheduled refill date, update inventory requirements at an indicated default store at which the prescription is to be refilled.

Those of ordinary skill in the art will also appreciate that substances other than prescription medication may also be included in a prescription alignment process. In one alternate embodiment of the prescription alignment system, a supply of a non-prescription substance may be aligned with one or more prescriptions. The aligned non-prescription substance may be, by way of example and not limitation, an over-the-counter medication (i.e., one that does not require a prescription from a physician) or a vitamin or other supplement.

Though the preferred embodiment of the prescription alignment system described herein assumes a customer purchasing a plurality of prescriptions from a retail pharmacy, the system as described to this point may be employed in mail-order pharmacies, specialty pharmacies, on-line pharmacies, etc., as described above with reference to FIG. 1A. As such, it will be clear to those of ordinary skill in the art that aligned prescriptions may be picked up (as at a retail pharmacy), but may also be amenable to delivery, for example via a parcel delivery service (e.g., a postal service, UPS®, FedEx®, etc.) or by courier. In such an instance, the user-interface 800-900 may include a means for selecting a method of receiving the aligned prescriptions, as well as an indication of the method selected. Where the customer has opted for delivery, the user-interface may include a means of selecting a default delivery address, and may further include means of selecting an alternate delivery address, for example for a single refill date on which the customer may be on vacation. Additionally, where a customer elects to receive the aligned prescriptions by delivery, the prescription alignment system may fill the prescriptions before the alignment date (or subsequent refill date) by a time period calculated such that the customer receives the prescriptions on the alignment date.

Providing an option for a customer to receive the aligned prescriptions via a delivery service such as UPS® or FedEx® may be advantageous to a pharmacy, as it may allow the pharmacy to centralize its filling services for a larger number of customers. This may reduce inventory distribution demands and allow reduced pharmacy staff, in addition to other efficiency gains. A large pharmacy chain having thousands of stores across a wide geographical area may be able, by virtue of a central filling facility, to deliver prescriptions to customers much more efficiently. It is, among other things, the fact that as aligned prescriptions, the facility need no longer fill individual prescriptions on separate dates and ship them at separate times that allows these efficiencies to be achieved. Additional efficiencies may be achieved in some instances where pharmacies, whether large or small, outsource the prescription-filling services to a third-party.

Figure 10:
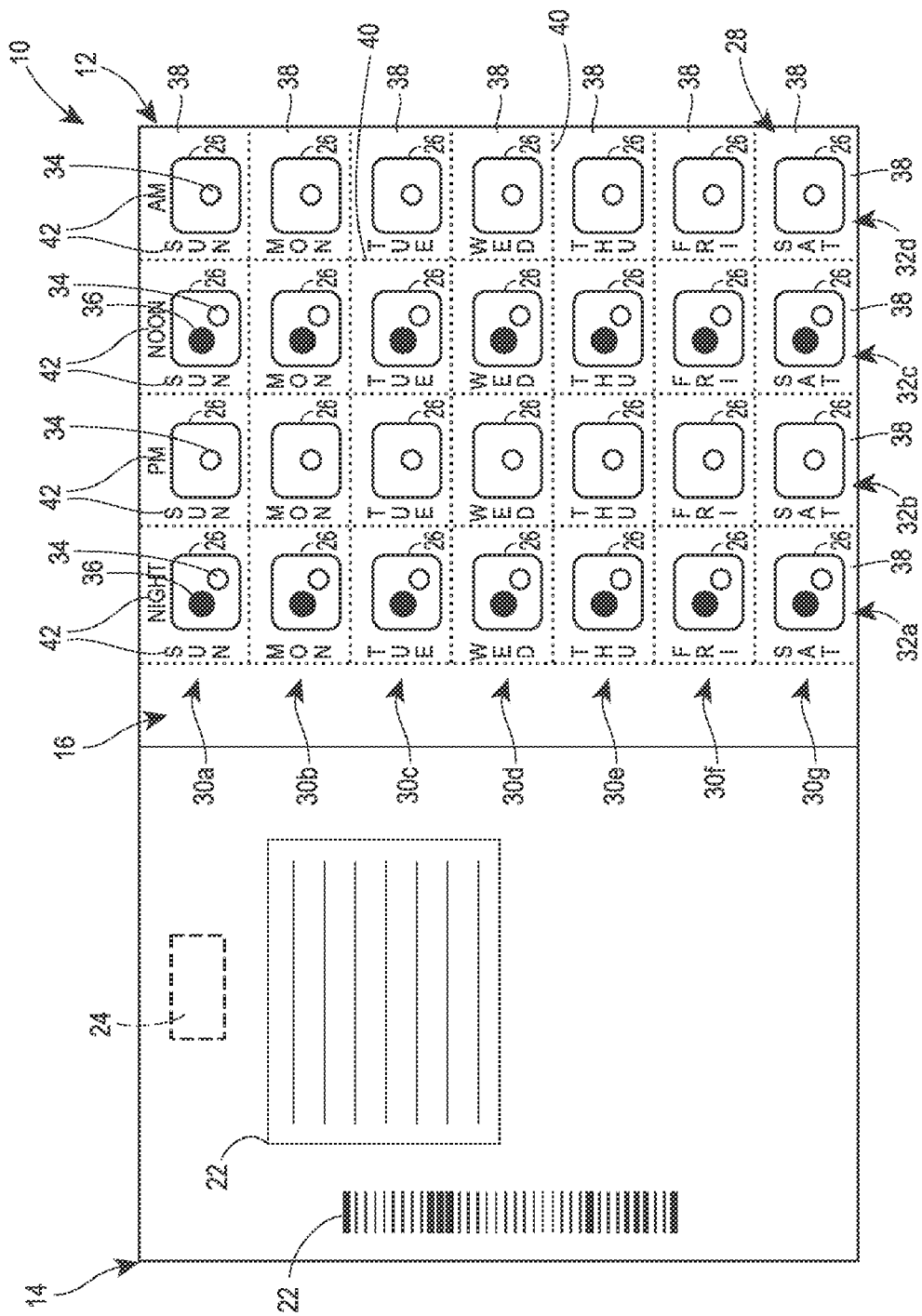
FIG. 10 illustrates a multi-dose package that may be used in the exemplary prescription alignment in accordance with the described embodiments.

In another alternate embodiment of the exemplary prescription alignment system, one or more of the prescriptions (or aligned non-prescription substances) may be dispensed in a multi-dose package such as a multi-dose pouch or, alternatively, the blister package shown in FIG. 10, and described in detail in provisional application 60/940,790, entitled "Multi-Dose Filling Machine and Process" and filed on May 30, 2007. FIG. 10 depicts one embodiment of a multi-dose product package 10. The product package 10 generally includes a multi-dose blister card 12 and a cover 14, connected by a spine 16. The cover 14 and spine 16 allow the package 10 to be closed similar to a book and may also contain identification information related to a prescription, the product stored in the multi-dose blister card 12, and/or the customer. It is noted that numerous alternative designs for the product package exist, such as, for example, a tri-fold design or a wallet style, where the blisters are arranged to nest with one another when the package is folded.

FIG. 10 shows the cover 14 includes an inside surface 18 carrying a patient identification label 20 and a product information storage device 22. The product information storage device 22 may include, for example, a bar code or a radio frequency identification (RFID) tag. Additionally, the package 10 may include a timer 24 such as an electronic timer for signaling to a patient, for example, when to take his/her medication. The timer 24 is depicted in phantom in FIG. 10 such that it may be understood that the timer 24 may be retained between multiple plies of the material forming the cover 14 such that a visual indicator such as a blinking light may be disposed on an outside surface of the cover 14. The timer 24 may include an audible indicator such as a speaker for emitting a beep, for example. Although not depicted, it should be appreciated that alternate embodiments of the package 10 may include either or both of the patient identification label 20 and the product information storage device 22 on an outside surface of the cover 14. So configured, such information may be readily attainable without having to open the cover 14.

The multi-dose blister card 12 of the package 10 depicted in FIG. 10 includes a plurality of blisters 26 arranged in a matrix 28. Additionally, the multi-dose blister card 12 includes a removable foil-backing material (not shown) on the backside of the blister card 12 to seal the blisters 26. The matrix 28 depicted in FIG. 10 includes a four-by-seven matrix, signifying the seven days of the week and the four general times of the day. More particularly, the matrix 28 includes seven rows 30a-30g, each row assigned to one day of the week, i.e., "Sunday," "Monday," "Tuesday," "Wednesday," "Thursday," "Friday," and "Saturday." Additionally, the matrix 28 includes four columns 32a-32d, each column assigned to a distinct time of the day, i.e., "AM," "Noon," "PM," and "Night."

Accordingly, the multi-dose blister card 12 of FIG. 10 includes twenty-eight blisters 26, each containing a specified dose of one or more medications for ingestion on that particular day, at that particular time. For example, as depicted, the blister 26 located at row 30a and column 32d, which corresponds to "Sunday," "AM," includes a single tablet 34. Thus, the patient that has been prescribed the multi-dose blister card 12 knows to ingest tablet 34 during the "AM" or morning on "Sunday." In contrast, blister 26 located at row 30a and column 32c, which corresponds to "Sunday," "Noon," includes one tablet 34 and one table 36. Accordingly, the patient knows to ingest tablet 34 and tablet 36 at "Noon" or with lunch, on "Sunday." The multi-dose blister card 12 depicted in FIG. 10 is only one example of how various medications may be stored for a particular patient. It should be appreciated that the blisters 26 of the multi-dose blister card 12 may contain generally any number of tablets for ingestion by the particular patient, in accordance with generally any prescription(s). The only limitation on the number of tablets or variations of prescriptions stored by the multi-dose blister card 12 is the size of the individual blisters 26. Nevertheless, it is foreseeable that the principles of the present invention may be applied to multi-dose blister cards having different quantities of blisters for different day supplies, and blisters of generally any size and configuration.

Additionally, the product package 10 is designed to contain one or more prescriptions for a single week, i.e., seven days. Thus, a patient with a prescription that lasts more than a week may require multiple product packages, where each package 10 is assigned to a particular week.

The multi-dose blister card 12 includes a plurality of cells 38 that constitute the rows 30a-30g and columns 32a-32d of the matrix 26. Thus, each cell 38 accommodates a single blister 26. Additionally, in the disclosed embodiment, each of the cells 38 may be separated by perforated seams 40. So configured, a patient may remove one or more of the cells 38 including the cells' 38 respective blisters 26 from the multi-dose blister card 12. This allows the patient to discard empty blisters 26 and/or to transport one or more blisters 26 without having to transport the entire package 10. Alternate embodiments may not include perforated seams 40.

Additionally, as depicted in FIG. 10, each cell 38 includes indicia 42 indicating to the patient when to ingest the tablets stored in the particular blister 26. For example, the blister 26 located at row 30a and column 32d includes indicia 42 identifying "SUN" for Sunday, and "Night" for night-time. The remaining cells 38 have similar indicia. Accordingly, while the multi-dose blister card 12 is unique for every patient, there may be many similarities from one patient's multi-dose blister card to the next. So configured, not necessarily every blister 26 must be filled for a specific prescription to be satisfied.

Further still, it is not necessary that each of the prescriptions selected for alignment be dispensed in multi-dose packaging. If each of the prescriptions selected for alignment is dispensed in multi-dose packaging, it is not required that they be dispensed in a single multi-dose package. For example, medications that may have interactions detrimental to a patient when taken in temporal proximity to each other may be packaged in separate packaging to prevent their accidental ingestion together. The user-interface 800-900 may include a method of selecting (not shown) which prescriptions to include in a multi-dose package, or otherwise allow a pharmacist to indicate how to divide prescriptions (or non-prescription substances) one or more multi-dose packages.

While the preceding paragraphs describe several exemplary embodiments of a prescription alignment system, the various embodiments described are not intended to limit the invention to the individual embodiments. Various aspects of the alternate embodiments may be combined in varying ways to create the system and method that best suits the pharmacy implementing the system and method, the pharmacy's customers, and the regulatory environment in which the pharmacy operates.

What is claimed:

1. A computer-readable storage medium having machine-executable instructions stored thereon, the instructions operable, when executed by a processor, to cause the processor to: receive a selection of a plurality of prescriptions to align; determine, for each of the plurality of selected prescriptions, a next fill date, wherein the next fill date is the date the prescription was last filled, incremented by a pre-alignment day supply for the prescription; compute at least one alignment date corresponding to at least one of a quickest alignment option, a lowest cost alignment option, or a medication status alignment option, wherein the medication status alignment option is based on a status of at least one medication as a generic medication or a brand name medication; compute an alignment cost for at least one of the quickest alignment option, the lowest cost alignment option, the medication status alignment option, or one or more custom alignment options; receive a plurality of alignment date selections, each corresponding to one of the quickest alignment option, the lowest cost alignment option, the medication status alignment option, or a one of the one or more custom alignment options, wherein each selected alignment date is selected for at least two prescriptions; determine for each of the plurality of selected prescriptions any intervening fill dates for the prescription between the current date and the one or more alignment dates associated with the selected prescription; and determine for each of the plurality of selected prescriptions whether each of the alignment dates requires a reduced fill and, for each prescription for which it is determined that a reduced fill is required, further determine:
(a) a reduced-fill date on which the reduced fill occurs; (b) a reduced-fill day supply for the reduced fill; and (c) a reduced-fill cost for the reduced fill; (d) wherein the reduced-fill date for each prescription requiring a reduced fill is the intervening fill date for the prescription that is closest to the selected alignment date; and (e) wherein the reduced-fill day supply for the prescription is the number of days from the reduced-fill date to the selected alignment date.

2. The computer-readable storage medium of claim 1, the instructions further operable to cause the processor to: store, for each of a plurality of customers, a customer record comprising a customer identifier indicative of a customer, and one or more prescriptions; retrieve one or more customer records; retrieve the one or more prescriptions associated with each of the one or more retrieved records; determine whether each of the retrieved prescriptions is eligible for prescription alignment; determine for each of the at least one customer records whether prescription alignment would violate rules of a third-party payor associated with the indicated customer; and determine, for each of the at least one customer records, whether prescription alignment would violate applicable regulations in effect pertaining to the prescription alignment.

3. The computer-readable storage medium of claim 1, the instructions further operable to cause the processor to: determine a benchmark date for the plurality of selected prescriptions, the benchmark date associated with a benchmark prescription; and repeat the following steps until an alignment date is selected: (a) compare the benchmark date to the latest of the plurality of determined next fill dates; (b) select the benchmark date as the selected alignment date if the benchmark date is later than or the same as the latest of the determined next fill dates; and (c) select as the benchmark date, if the benchmark date is earlier than the latest of the determined next fill dates, a subsequent next fill date for the benchmark prescription.

4. The computer-readable storage medium of claim 3, wherein the instructions operable to determine a benchmark date corresponding to the quickest alignment option comprise instructions operable to select the latest of the plurality of determined next fill dates as the benchmark date.

5. The computer-readable storage medium of claim 3 wherein the instructions operable to determine a benchmark date corresponding to the lowest cost alignment option comprise instructions operable to: group the plurality of selected prescriptions by next fill date, wherein a prescription group may comprise a single prescription or a plurality of prescriptions; determine a pre-alignment cost for each of the plurality of selected prescriptions; calculate the total of the pre-alignment costs for each of the prescription groups; find the one or more prescription groups having the highest total pre-alignment cost; select, where only one prescription group has the highest total pre-alignment cost, a next fill date for that prescription group, as the benchmark date; and select, where more than one prescription group has the highest total pre-alignment cost, the latest of the next fill dates corresponding to the prescription groups having the highest total pre-alignment cost.

6. The computer-readable storage medium of claim 5 wherein each prescription of a group of prescriptions constitutes a benchmark prescription and further wherein instructions operable to select a subsequent next fill date for the benchmark prescription as the benchmark date for the benchmark prescription further comprise instructions operable to: repeat, for each prescription of the one or more groups of prescriptions having the highest total pre-alignment cost, each of the following steps until each prescription of the one or more groups of prescriptions having the highest total pre-alignment cost has a benchmark date later than or the same as the latest next fill date: (i) determine a subsequent next fill date for the prescription, wherein the subsequent next fill date for the prescription is determined according to the pre-alignment day supply for the prescription; (ii) compare the determined subsequent next fill date to the latest next fill date; and (iii) set the benchmark date for the prescription to the determined subsequent next fill date if the determined subsequent next fill date is later than or the same as the latest next fill date.

7. The computer-readable storage medium of claim 6, further comprising instructions operable to cause the processor to select as the alignment date, where each of the benchmark prescriptions has a different cost than each other benchmark prescription, the benchmark date of the benchmark prescription having the highest cost.

8. The computer-readable storage medium of claim 6, further comprising instructions operable to cause the processor to select as the alignment date, where each of the benchmark prescriptions has the same cost as each other benchmark prescription, the benchmark date of the benchmark prescription having the earliest benchmark date after the latest next fill date.

9. A user-interface employed in a system for aligning a plurality of pharmaceutical prescriptions to a plurality of alignment dates, the user-interface comprising:
   one or more user-interface screens being generated and displayed by a computer,
   one or more controls indicating a plurality of prescriptions selected for alignment and allowing a user to edit the selected prescriptions;
   an indication, for each of the plurality of selected prescriptions, of each of a last fill date, a quantity supplied, a pre-alignment day supply, and a pre-alignment cost;
   one or more controls indicating a plurality of prescription alignment dates and allowing the user to edit one or more of the plurality of prescription alignment dates;
   an indication of zero or more of the plurality of selected prescriptions that will require a reduced fill, a reduced-fill date for each required reduced fill, a reduced-fill day supply to be provided on each reduced-fill date, and a reduced-fill cost of each required reduced fill;
   an indication of a post-alignment day supply for each prescription at each alignment date; and
   a control indicating a post-alignment cost at each alignment date and allowing the user to edit the post-alignment day supply for each of the alignedprescriptions;
   wherein a printable version of the displayed information may be generated;
   wherein the prescription alignment may be confirmed.

10. The user-interface of claim 9 wherein the control indicating each of the prescription alignment dates initially reflects either an alignment date associated with a lowest cost option or an alignment date associated with a fastest alignment option, and wherein the control indicating each of the alignment dates may be toggled between the lowest cost option and the fastest alignment option, or manually edited.

* * * * *